United States Patent
Serteyn et al.

(10) Patent No.: US 9,695,476 B2
(45) Date of Patent: Jul. 4, 2017

(54) METHOD FOR THE DIAGNOSIS OF OSTEOCHONDROSIS

(71) Applicants: Universite de Liege, Angleur (BE); Skuldtech s.a., Montpellier (FR)

(72) Inventors: Didier Serteyn, Tavier (BE); Charlotte Sandersen, Dolembreux (BE); Jean-Philippe Lejeune, Herstal (BE); David Piquemal, St. Christol les Ales (FR)

(73) Assignees: UNIVERSITE DE LIEGE, Angleur (BE); SKULDTECH S.A., Montpellier (FR)

( * ) Notice: Subject to any disclaimer, the term of this patent is extended or adjusted under 35 U.S.C. 154(b) by 628 days.

(21) Appl. No.: 14/049,713

(22) Filed: Oct. 9, 2013

(65) Prior Publication Data

US 2014/0134627 A1 May 15, 2014

(30) Foreign Application Priority Data

Oct. 9, 2012 (EP) ..................................... 12187726

(51) Int. Cl.
*C12Q 1/68* (2006.01)

(52) U.S. Cl.
CPC ..... *C12Q 1/6883* (2013.01); *C12Q 2600/158* (2013.01)

(58) Field of Classification Search
None
See application file for complete search history.

(56) References Cited

PUBLICATIONS

Serteyn et al. (J. Orthopedic Research, 2010, p. 965-970).*
Didier Serteyn et al. "Gene expression profiling from leukocytes of horses affected by osteochondrosis", in *Journal of Orthopaedic Research*, Online Jan. 2010 / Jul. 2010, pp. 965-970.
Tara L. Riddick et al. "Gene and protein expression of cartilage canal and osteochondral junction chondrocytes and full-thickness cartilage in early equine osteochondrosis", in *The Veterinary Journal*, vol. 194, n° 3, pp. 319-325 (2012).
Michiko Mirams et al. "Altered gene expression in early osteochondrosis lesions", in *Journal of Orthopaedic Research*, vol. 27, n° 4, pp. 452-457 (2009).
S. Ekman et al. "Third International Workshop on Equine Osteochondrosis, Stockholm, May 29-30, 2008", in *Equine Veterinary Journal*, vol. 41, n°5, pp. 504-507 (2009).
K.E. Glaser et al. "Development of a novel equine whole transcript oligonucleotide GeneChip microarray and its use in gene expression profiling of normal articular-epiphyseal cartilage", in *Equine Veterinary Journal*, vol. 41, n° 7, pp. 663-670 (2009).
Needleman and Wunsch "A general method applicable to the search for similarities in the Amino acid sequence of two proteins", in *J Mol. Biol.*, vol. 48, pp. 443-453, (1970).
E. Meyers and W.Miller "Optimal alignments in linear space", in *CABIOS*, vol. 4 (1), pp. 11-17, (1988).
Schmittgen and Livak "Analyzing real-time PCR data by the comparative Ct method", in *Nature Protocols*, vol. 3(6), pp. 1101-1108 (2008).
Livak, KJ and Schmittgen TD "Analysis of relative gene expression data using real-time quantitative PCR and the 2 Method", In *Methods*, vol. 25(4), pp. 402-408 (2001).

\* cited by examiner

*Primary Examiner* — Stephanie K Mummert
(74) *Attorney, Agent, or Firm* — Jacobson Holman, PLLC.

(57) ABSTRACT

The invention provides an in vitro method or assay for the diagnosis of osteochondrosis or prediction of the likelihood of its onset in a terrestrian mammal, comprising measuring the expression level of a marker in a sample obtained from said terrestrian mammal and comparing said expression level to the expression level of said marker measured in a sample obtained from one or more terrestrian mammals of the same species not affected by osteochondrosis, wherein the marker is ApoB-3G, and wherein an increase in the expression level of ApoB-3G is indicative of osteochondrosis. The invention also provides a diagnostic kit for use in said method, which comprises at least one agent, which binds specifically to the product of the gene of the respective marker and which can be used to determine the expression level of said marker, wherein the marker is ApoB-3G.

16 Claims, 2 Drawing Sheets

METHOD FOR THE DIAGNOSIS OF OSTEOCHONDROSIS

The present invention relates to an in vitro method for the diagnosis of osteochondrosis in terrestrial mammals based on the measurement of the expression level of markers in samples obtained from said terrestrial mammals. The present invention further relates to a kit for use in said method.

Osteochondrosis (OC) is a family of orthopedic diseases of the joint affecting rapidly growing animals. OC may occur for example in horses and dogs. OC seriously affects the animals' ability to perform athletically and often represents a personal and economic loss to the owner.

Several processes are believed to be a starting point for the development of OC, for example, abnormal chondrocyte differentiation, formation of a fragile cartilage, failure of blood supply to growing cartilage, and subchondral bone necrosis.

Abnormal chondrocyte differentiation is believed to lead to altered enchondral ossification resulting in irregularities in thickness of the epiphyseal cartilage. This mechanism of dyschondroplasia may affect different joints, particularly the metacarpo- and metatarso-phalangeal joints (fetlock joint), the lateral ridge of the talus or the tibial cochlea in the tibio-tarsal joint (hock joint), and the lateral ridge of the trochlea in femoro-patellar joints (stifle joint).

The ultimate cause for OC appears to be multifactorial. Possible etiologic factors include skeletal growth rates, nutrition, endocrinologic factors, physical exercise of the animal, biomechanics, and genetic effects.

The time course of the development of OC lesions seems to be joint dependent. In horses, it has been shown that OC lesions appear rapidly after birth but most of these lesions regress in the following months up to the age of 1 year. OC lesions develop in the hock joint in the first month of life. Followed by a period of regression they seem to be stationary after the fifth month of life. In the stifle joint, this process is more delayed and most OC lesions develop around the fifth month of age, thereafter they can decrease to become stationary at the age of eleven months.

OC is currently diagnosed by radiography. However, all possibly affected joints shall be radiographed. Moreover, it is frequent that some unusual localizations are not diagnosed by this technique. Furthermore, radiography is not sensitive enough to detect early lesions affecting only the cartilage. Some lesions can be detected by ultrasound but often some parts of the joint are not accessible by echography. Therefore there is a need for another approach for the diagnosis of OC.

It is known that OC is associated with changes in the transcription profile of a number of genetic markers in leukocytes of horses, which are on average 2.5 years old (Serteyn et al., Journal of Orthopedic research, July 2010). For example, it has been shown that the markers ApoB-3G, ISG17, WASH1 and RUSC2 are underexpressed in leukocytes of horses, which are affected by OC and which are on average 2.5 years old, and that the marker Hp is overexpressed in leukocytes of those horses. However, there is so far no information on genetic markers for OC in young animals.

It is an object of the present invention to provide a minimally-invasive method for the diagnosis of OC in terrestrial mammals. The method should be able to reliably diagnose OC at a relatively early stage, particularly in young animals. Ideally, the method should be also able to predict the onset of OC in animals. Furthermore, the method should be able to diagnose which joint is affected by OC.

In the present invention, it has been found that the expression level of certain markers is an indicator for osteochondrosis in terrestrial mammals. In particular, it has been found that the expression level of the marker ApoB3-G is increased in terrestrial mammals affected by osteochondrosis compared to healthy terrestrial mammals of the same species.

The present invention therefore provides an in vitro method or assay for the diagnosis of osteochondrosis or the prediction of the likelihood of its onset in a terrestrial mammal, comprising the steps a) measuring the expression level of a marker in a sample obtained from said terrestrial mammal with an agent that can be used to determine the expression level of said marker, and b) comparing the expression level measured in step a) to the expression level of said marker measured in a sample obtained from one or more terrestrial mammals of the same species not affected by osteochondrosis, characterized in that the marker is ApoB-3G, wherein an increase in the expression level of ApoB-3G is indicative of osteochondrosis.

The skilled person understands that the increase or decrease in the expression level of a marker used herein is in comparison with the expression level of the respective marker in healthy terrestrial mammals.

As used herein, a "marker" is a gene or a product of a gene, and the "expression level" is any measure for the degree to which the product of the gene is produced. A "product of a gene" as used herein may be mRNA or protein, or fragments thereof. Further, a "product of a gene" may be also a cDNA obtained from the respective mRNA. The skilled person understands that the wording "an agent that can be used to determine the expression level of said marker" means that the agent is suitable for or adapted for said purpose, and that said agent is specific for the respective marker.

In alternative embodiments of the present invention in vitro methods or assays are provided for the diagnosis of osteochondrosis or the prediction of the likelihood of its onset in a terrestrial mammal, comprising the steps a) measuring the expression level of a marker in a sample obtained from said terrestrial mammal with an agent that can be used to determine the expression level of said marker, and b) comparing the expression level measured in step a) to the expression level of said marker measured in a sample obtained from one or more terrestrial mammals of the same species not affected by osteochondrosis, characterized in that the marker is selected from the list consisting of cdh1, pcolce2, tcf4, src, sdc1, mhc1 and gja1, wherein a change in the expression level of the respective maker compared to healthy terrestrial mammal is indicative of osteochondrosis.

That is, in each of the preferred embodiments described in this application the measuring of the expression level of the marker "ApoB-3G" may be replaced by the measuring of the expression level of any one of the following markers: cdh1, pcolce2, tcf4, src, sdc1, mhc1 and gja1. This means that in a first alternative embodiment the measuring of the expression level of the marker "ApoB-3G" may be replaced by the measuring of the expression level of the marker cdh1. In a second alternative embodiment the measuring of the expression level of the marker "ApoB-3G" may be replaced by the measuring of the expression level of the marker pcolce2. In a third alternative embodiment the measuring of the expression level of the marker "ApoB-3G" may be replaced by the measuring of the expression level of the marker tcf4. In a fourth alternative embodiment the measuring of the expression level of the marker "ApoB-3G" may be replaced by the measuring of the expression level of the marker src. In a fifth alternative embodiment the measuring of the expression level of the marker "ApoB-3G" may be replaced by the measuring of the expression level of the marker sdc1. In a sixth alternative embodiment the measuring of the expression level of the marker "ApoB-3G" may be replaced by the measuring of the expression level of the marker mhc1. In an seventh alternative embodiment the measuring of the expression level of the marker "ApoB-3G" may be replaced by the measuring of the expression level of the marker gja1.

For the purpose of the present invention, a "sample" is any sampling of cells, tissues, or body fluids, in which the expression level of a marker can be determined. Examples of such samples include blood, lymph, urine, biopsies, or bone marrow. Samples may be obtained from a subject by various techniques, for example, by scraping a body area or by using a needle to aspirate a body fluid. Preferably, the sample is obtained in a non-invasive or minimally invasive manner. In a preferred embodiment of the inventive method, the sample is a blood sample, which can be whole blood, blood serum or plasma.

The expression level may be determined by measuring, for example, the amount of mRNA or the amount of protein present in the sample. The expression level of the marker can be determined, for example, with an assay for global gene expression in a sample (e.g. using a microarray for gene expression profiling analysis), or by specific detection, for example by quantitative PCR, real time quantitative PCR, or Western blot. In particular, the measurement of the expression level of a marker in a sample obtained from said terrestrian mammal will be carried out with an agent that can be used to determine the expression level of said marker. Said agent may be primers or primer sets to specifically reverse transcribe and amplify the mRNA of the respective marker or antibody specifically detecting the marker in its protein form, i.e. the marker as a protein.

That is, in a preferred embodiment, the expression level of a given marker is determined by isolating mRNA from a blood sample obtained from a subject, reverse-transcribing the mRNA into cDNA, and quantifying the amount of cDNA specific for the marker by PCR-based techniques. To account for the variance in the total amount of mRNA in a given sample compared to other samples, the amount of cDNA for a specific marker is normalized to the amount of cDNA for a housekeeping gene. Suitable housekeeping genes for this purpose are those, whose expression level do not differ between subjects affected by osteochondrosis and healthy subjects. Examples for housekeeping genes are Axin1, CtBP1, and CD44.

In another preferred embodiment the expression level of a given marker is determined by isolating protein from a blood sample obtained from a subject, and quantifying the amount of protein specific for the marker by detection of said protein with a specific antibody, for example, by Western blot. To account for the variance in the total amount of protein in a given sample compared to other samples, the amount of protein for a specific marker is normalized to the amount of protein for a housekeeping gene, such as those mentioned above.

The expression level in the sample to be studied is compared to a reference value, which is the expression level found in a sample from a subject of the same species not affected by osteochondrosis. Preferably, the reference value is the average expression level found in samples from a population of subjects of the same species not affected by osteochondrosis. Preferably, the average expression level found in samples from a population of subjects of the same species is determined once and then stored in a database for reference. Preferably, the reference value is measured in samples obtained from one or more subjects of the same species and the same age group as the subject, in which osteochondrosis is to be diagnosed.

The expression level found in the sample is considered to be increased or decreased if the difference of this expression level to the reference value is statistically significant. If the difference is not considered statistically significant, the expression level is considered unchanged. The difference may be considered to be statistically significant if its absolute value exceeds a predetermined threshold value. This threshold value can, for example, be the standard deviation of the expression level found in samples from a population of subjects not affected by osteochondrosis as indicated in table 2 and FIG. 2. For example, in case the method of qPCR is used, the data obtained are analyzed using the 2(-Delta Delta C(T)) (ΔΔCt) method (Livak, K J and Schmittgen T D, *Methods,* 2001 December; 25 (4); pages 402-408). The ΔCt values are determined for all target genes by subtracting the Ct values from the mean of the Ct values of the reference (housekeeping) genes. Values are indicated in table 2 and FIG. 2.

In addition to ApoB-3G, it has also been found that the expression levels of each of the markers Dsh1, Foxl1, Hp, ISG17, Mark2, PPP2R1A-a, PPP2R1A-b, RUSC2 and WASH1 are indicative of osteochondrosis. Hence, the present invention also provides a method, in which the expression levels of one or more of these markers are measured in addition to the expression level of ApoB-3G. The expression level of each individual marker is compared to the expression level of said marker in subjects not affected by osteochondrosis. In this method osteochondrosis is indicated by a decrease in the expression levels of Dsh1, Foxl1, Hp, ISG17, Mark2 and/or RUSC2, and/or an increase or decrease in the expression level of PPP2R1A-a, PPP2R1A-b and/or WASH1.

The reliability of the inventive method will increase with the number of markers investigated. Hence, in addition to measuring the expression level of ApoB-3G, the method preferably comprises measuring the expression levels of at least one, preferably two, three, four, fife, six, seven, eight and most preferably all of said additional markers Dsh1, Foxl1, Hp, ISG17, Mark2, PPP2R1A-a, PPP2R1A-b, RUSC2 and WASH1.

In a particularly preferred embodiment, the method comprises measuring the expression levels of the markers ApoB-3G, Dsh1, Foxl1, Hp, PPP2R1A-a, RUSC2 and WASH1. In an even more preferred embodiment, the method comprises measuring the expression levels of the markers ApoB-3G, Dsh1, Foxl1, Hp, ISG17, Mark2, PPP2R1A-a, PPP2R1A-b, RUSC2 and WASH1.

It has further surprisingly been found in the present invention that the pattern of expression levels of the aforementioned markers is an indicator for the joint, which is affected by osteochondrosis. The present invention therefore also provides an in vitro method or assay wherein the expression levels of at least one, two, several or all of the additional markers Dsh1, Foxl1, Hp, PPP2R1A-a, RUSC2 and WASH1 are measured, wherein the expression levels of Dsh1, Foxl1, Hp, PPP2R1A-a, RUSC2 and WASH1 are further used to diagnose and/or predict whether the fetlock joint, the hock joint or the stifle joint is or will be affected by osteochondrosis. In a particularly preferred method the expression levels of at least the markers of one of the following marker combinations are measured: Foxl1 and WASH1; or Foxl1 and PPP2R1A-a.

The joints, which can be preferably distinguished with the inventive method are the metacarpo- and metatarso-phalangeal joint (fetlock joint), the tibio-tarsal joint (hock joint) and the femoro-patellar joint (stifle joint).

In another preferred embodiment of the present invention the expression levels of at least one, two, several or all of the additional markers Dsh1, Foxl1, Hp, PPP2R1A-a, RUSC2 and WASH1, are measured, an increase in the expression level of each PPP2R1A-a and WASH1, a decrease in the expression level of each Dsh1, Foxl1, Hp and RUSC2 is indicative of affection of the fetlock joint;

a decrease in the expression level of each Dsh1, Hp, PPP2R1A-a, RUSC2 and WASH1 and no change in the expression level of Foxl1 is indicative of affection of the hock joint; and a decrease in the expression level of each Dsh1, Foxl1, Hp, PPP2R1A-a, RUSC2 and WASH1 is indicative of affection of the stifle joint. In a particularly preferred method the expression levels of at least the markers of one of the following marker combinations are measured: Foxl1 and WASH1; or Foxl1 and PPP2R1A-a.

In a further preferred embodiment of the method of the present invention the expression levels of at least one, two, several or all of the additional markers Dsh1, Foxl1, Hp, Mark2, PPP2R1A-a, WASH1, ISG17, PPP2R1A-b and RUSC2 are measured, wherein the expression levels of Dsh1, Foxl1, Hp, Mark2, PPP2R1A-a, WASH1, ISG17, PPP2R1A-b and RUSC2 are further used to diagnose and/or predict whether the fetlock joint, the hock joint or the stifle joint is or will be affected by osteochondrosis. In a particularly preferred method the expression levels of at least the markers of one of the following marker combinations are measured: Foxl1 and WASH1; or Foxl1 and PPP2R1A-a; or Foxl1 and PPP2R1A-b.

In another preferred embodiment of the present invention the expression levels of at least one, two, several or all of the additional markers Dsh1, Foxl1, Hp, Mark2, PPP2R1A-a, WASH1, ISG17, PPP2R1A-b and RUSC2 are measured, wherein an increase in the expression level of each PPP2R1A-a, PPP2R1A-b and WASH1, a decrease in the expression level of each Dsh1, Foxl1, Hp, Mark2 and RUSC2 and no change in the expression level of ISG17 is indicative of affection of the fetlock joint;

a decrease in the expression level of each Dsh1, Hp, ISG17, Mark2, PPP2R1A-a, PPP2R1A-b, RUSC2 and WASH1 and no change in the expression level of Foxl1 is indicative of affection of the hock joint; and a decrease in the expression level of each Dsh1, Foxl1, Hp, ISG17, Mark2, PPP2R1A-a, PPP2R1A-b, RUSC2 and WASH1 is indicative of affection of the stifle joint. In a particularly preferred method the expression levels of at least the markers of one of the following marker combinations are measured: Foxl1 and WASH1; or Foxl1 and PPP2R1A-a; or Foxl1 and PPP2R1A-b.

This means that for example the expression level of one of the following markers are measured and further used to diagnose and/or predict whether the fetlock joint, the hock joint or the stifle joint is or will be affected by osteochondrosis: Dsh1, Foxl1, Hp, Mark2, PPP2R1A-a, WASH1, ISG17, PPP2R1A-b and RUSC2. Further, the expression level of any one of the following sets of markers are measured and further used to diagnose and/or predict whether the fetlock joint, the hock joint or the stifle joint is or will be affected by osteochondrosis:

Dsh1, Foxl1; Dsh1, Hp; Dsh1, Mark2; Dsh1, PPP2R1A-a; Dsh1, WASH1; Dsh1, ISG17; Dsh1, PPP2R1A-b; Dsh1, RUSC2; Foxl1, Hp; Foxl1, Mark2; Foxl1, PPP2R1A-a; Foxl1, WASH1; Foxl1, ISG17; Foxl1, PPP2R1A-b; Foxl1, RUSC2; Hp, Mark2; Hp, PPP2R1A-a; Hp, WASH1; Hp, ISG17; Hp, PPP2R1A-b; Hp, RUSC2; Mark2, PPP2R1A-a; Mark2, WASH1; Mark2, ISG17; Mark2, PPP2R1A-b; Mark2, RUSC2; PPP2R1A-a, WASH1; PPP2R1A-a, ISG17; PPP2R1A-a, PPP2R1A-b; PPP2R1A-a, RUSC2;

Dsh1, Foxl1, Hp;
Dsh1, Foxl1, RUSC2;
Dsh1, Foxl1, PPP2R1A-a;
Dsh1, Foxl1, WASH1;
Foxl1, Hp, RUSC2;
Foxl1, Hp, PPP2R1A-a;
Foxl1, Hp, WASH1;
Hp, RUSC2, PPP2R1A-a;
Hp, RUSC2, WASH1;
RUSC2, PPP2R1A-a, WASH1;
Dsh1, Foxl1, Hp, RUSC2;
Dsh1, Foxl1, Hp, PPP2R1A-a;
Dsh1, Foxl1, Hp, WASH1;
Foxl1, Hp, RUSC2, PPP2R1A-a;
Foxl1, Hp, RUSC2, WASH1;
Hp, RUSC2, PPP2R1A-a, WASH1;
Dsh1, Foxl1, PPP2R1A-a, WASH1;
Dsh1, Foxl1, RUSC2, WASH1;
Dsh1, Foxl1, RUSC2, PPP2R1A-a;
Dsh1, Foxl1, Hp, WASH1;
Dsh1, Foxl1, Hp, PPP2R1A-a;
Dsh1, RUSC2, PPP2R1A-a, WASH1;
Dsh1, Foxl1, Hp, WASH1;
Dsh1, Hp, PPP2R1A-a, WASH1;
Dsh1, Hp, RUSC2, WASH1;
Dsh1, Hp, RUSC2, PPP2R1A-a;
Dsh1, Hp, RUSC2, WASH1;
Dsh1, Hp, RUSC2, PPP2R1A-a;
Dsh1, Foxl1, Hp, RUSC2, PPP2R1A-a;
Dsh1, Foxl1, Hp, RUSC2, WASH1;
Dsh1, Foxl1, Hp, PPP2R1A-a, WASH1;
Dsh1, Foxl1, RUSC2, PPP2R1A-a, WASH1;
Dsh1, Hp, RUSC2, PPP2R1A-a, WASH1;
Foxl1, Hp, RUSC2, PPP2R1A-a, WASH1;
Dsh1, Foxl1, Hp, RUSC2, PPP2R1A-a, WASH1.

It is particularly preferred that the expression levels of at least the markers of one of the following marker combinations are measured:
Foxl1, WASH1; or
Foxl1, PPP2R1A-a; or
Foxl1, PPP2R1A-b.

In another preferred embodiment of the present invention the expression levels of the additional markers Dsh1, Foxl1, Hp, PPP2R1A-a, RUSC2 and WASH1 are measured, wherein a decrease in the expression level of each Dsh1, Foxl1, Hp, PPP2R1A-a, RUSC2 and WASH1 is indicative of affection of the stifle joint.

In a further preferred embodiment of the present invention the expression levels of the additional markers Dsh1, Foxl1, Hp, ISG17, Mark2, PPP2R1A-a, PPP2R1A-b, RUSC2 and WASH1 are measured, wherein a decrease in the expression level of each Dsh1, Foxl1, Hp, ISG17, Mark2, PPP2R1A-a, PPP2R1A-b, RUSC2 and WASH1 is indicative of affection of the stifle joint.

In a particularly preferred embodiment the expression levels of any one or more or all of the following markers are measured and further used to diagnose and/or predict whether the fetlock joint, the hock joint or the stifle joint is or will be affected by osteochondrosis; wherein the degree of expression of the respective marker as given in the following table compared to the normal expression indicates which joint is or will be affected by osteochondrosis:

|  | fetlock | hock | stifle |
|---|---|---|---|
|  | expression level in % compared to normal expression level | | |
| Dsh1 | 90-50% | 90-50% | <50% |
| Foxl1 | <80% | 120-80% | <80% |
| Hp | 80-20% | <20% | 80-20% |
| ISG17 | 130-70% | <50% | <50% |
| Mark2 | 90-60% | 90-60% | <60% |
| PPP2R1A-a | >110% | 90-30% | <30% |
| PPP2R1A-b | >110% | 90-30% | <30% |
| RUSC2 | 90-40% | <40% | <40% |
| WASH1 | >110% | 90-60% | <60% |

The method of the present invention is used for the diagnosis of osteochondrosis in terrestrial mammals, preferably in terrestrial mammals of the order of Carnivora, Artiodactyla, and Perissodactyla. It is particularly preferred to use the method for the diagnosis of ostechondrosis for horse (*Equus* sp.), cattle (*Bos* sp.), pigs (*Sus* sp.), cats (*Felis* sp.) and dogs (*Canis* sp.), further preferred *Equus* sp., most preferred *Equus caballus*.

The method of the present invention can be used to diagnose osteochondrosis at a very early stage. Preferably the method of the present invention is used to predict osteochondrosis at a stage, at which it is not possible to reliably diagnose osteochondrosis by other methods known in the art, for example by radiography.

The method of the present invention therefore offers the possibility of predicting the likelihood of the onset of osteochondrosis as well.

Preferably, the method is used for the diagnosis of osteochondrosis in young subjects. In the context of the present invention, a "young" animal is an animal that has not yet reached sexual maturity. Preferably, a "young" animal is an animal which is still growing rapidly. As an example and particularly preferred embodiment, the inventive method can be used to diagnose osteochondrosis in a horse (genus *Equus*, preferably *Equus caballus*), which is not more than twelve months old.

In a preferred embodiment the present invention therefore provides a method for the diagnosis of osteochondrosis in a horse (genus *Equus*, preferably *Equus caballus*), which is not more than twelve months old, by measuring the expression level of the marker ApoB-3G, wherein an increase in the expression level of ApoB-3G is indicative of osteochondrosis. As mentioned before, the step of measuring the expression level of ApoB-3G may be replaced by measuring the expression level of any of cdh1, pcolce2, tcf4, src, sdc1, mhc1 and gja1.

In another preferred embodiment the present invention provides a method for the diagnosis of osteochondrosis in a horse (genus *Equus*, preferably *Equus caballus*), which is not more than twelve months old, by additionally measuring the expression level of at least one of the markers Dsh1, Foxl1, Hp, ISG17, Mark2, PPP2R1A-a, PPP2R1A-b, RUSC2 and WASH1, wherein osteochondrosis is indicated by a decrease in the expression levels of Dsh1, Foxl1, Hp, ISG17, Mark2, and/or RUSC2, and/or an increase or decrease in the expression level of PPP2R1A-a, PPP2R1A-b and/or WASH1.

In yet another preferred embodiment the present invention provides a method for the diagnosis and/or prediction of which joint in a horse (genus *Equus*, preferably *Equus caballus*), which is not more than twelve months old, is or will be affected by osteochondrosis by additionally measuring the expression levels of at least one, two, several or all of the markers Dsh1, Foxl1, Hp, PPP2R1A-a, RUSC2 and WASH1. In this method, an increase in the expression level of each PPP2R1A-a and WASH1, a decrease in the expression level of each Dsh1, Foxl1, Hp and RUSC2 is indicative of affection of the fetlock joint;

a decrease in the expression level of each Dsh1, Hp, PPP2R1A-a, RUSC2 and WASH1 and no change in the expression level of Foxl1 is indicative of affection of the hock joint; and a decrease in the expression level of each Dsh1, Foxl1, Hp, PPP2R1A-a, RUSC2 and WASH1 is indicative of affection of the stifle joint.

In still another preferred embodiment the present invention provides a method for to the diagnosis and/or prediction of which joint in a horse (genus *Equus*, preferably *Equus caballus*), which is not more than twelve months old, is or will be affected by osteochondrosis by additionally measuring the expression levels of one or more or all of the markers Dsh1, Foxl1, Hp, Mark2, PPP2R1A-a, WASH1, ISG17, PPP2R1A-b and RUSC2. In this method, an increase in the expression level of each PPP2R1A-a, PPP2R1A-b and WASH1, a decrease in the expression level of each Dsh1, Foxl1, Hp, Mark2 and RUSC2 and no change in the expression level of ISG17 is indicative of affection of the fetlock joint;

a decrease in the expression level of each Dsh1, Hp, ISG17, Mark2, PPP2R1A-a, PPP2R1A-b, RUSC2 and WASH1 and no change in the expression level of Foxl1 is indicative of affection of the hock joint; and a decrease in the expression level of each Dsh1, Foxl1, Hp, ISG17, Mark2, PPP2R1A-a, PPP2R1A-b, RUSC2 and WASH1 is indicative of affection of the stifle joint.

The present invention also provides an in vitro method or assay for the prediction of the likelihood of the onset of osteochondrosis in a terrestrial mammal, comprising the steps a) measuring the expression level of two or more markers in a sample obtained from said terrestrial mammal, and b) comparing the expression level measured in step a) to the expression level of said marker measured in a sample obtained from one or more terrestrial mammals of the same species not affected by osteochondrosis, characterized in that at least one of the markers is ApoB-3G and the additional marker(s) is/are selected from the list consisting of Dsh1, Foxl1, Hp, ISG17, Mark2, PPP2R1A-a, PPP2R1A-b, RUSC2 and WASH1. In a preferred method the sample is a blood sample, which can be whole blood, blood serum or plasma. In a further preferred method of the present invention the terrestrial mammals are selected from the order of Carnivora, Artiodactyla and Perissodactyla. It is particularly preferred that the terrestrial mammals are selected from the group consisting of horse (*Equus* sp.), cattle (*Bos* sp.), pigs (*Sus* sp.), cats (*Felis* sp.) and dogs (*Canis* sp.), even more preferred horse (*Equus* sp., *Equus caballus*), and most preferred horse (*Equus* sp., *Equus caballus*) which is not more than 12 months old.

The present invention also relates to a diagnostic kit for use in the method described above. This kit facilitates the method comprising the steps of measuring the expression level of a marker in a sample obtained from a terrestrian mammal, and comparing said expression level to the expression level of said marker measured in samples obtained from one or more terrestrian mammals of the same species not affected by osteochondrosis.

The inventive diagnostic kit comprises at least one agent, which binds specifically to the product of the gene of the respective marker and which can be used to determine the expression level of said marker, wherein the marker is ApoB-3G. The product of a gene of a marker can be, for example, the protein, mRNA or cDNA corresponding to said marker. The diagnostic kit also comprises instructions for use to diagnose osteochondrosis according to method described above.

In alternative embodiments, the diagnostic kit comprises additional agent(s) each for measuring the expression level of a marker selected from the list consisting of pcolce2, tcf4, src, sdc1, mhc1 and gja1, wherein each additional agent binds specifically to the product of the gene of the respective marker and can be used to determine the expression level of the respective marker.

The kit optionally comprises additional agent(s) for measuring the expression level of one or more additional markers and/or for measuring the expression levels of one or more housekeeping genes. Said additional markers are suitable for the diagnosis of osteochondrosis or the prediction of the likelihood of its onset in a terrestrian mammal. Alternatively or in addition, said additional markers are suitable for to diagnose and/or predict whether the fetlock joint, the hock joint or the stifle joint is or will be affected by osteochondrosis.

In a further embodiment, the diagnostic kit further comprises additional agent(s) each for measuring the expression level of a marker selected from the list consisting of Dsh1, Foxl1, Hp, ISG17, Mark2, PPP2R1A-a, PPP2R1A-b, RUSC2 and WASH1, wherein each additional agent binds specifically to the product of the gene of the respective marker and can be used to determine the expression level of the respective marker.

Preferably, the diagnostic kit also comprises additional agent(s) for measuring the expression level of a housekeeping gene selected from the list consisting of Axin1, CtBP1 and CD44, wherein each additional agent binds specifically to the gene product of the respective housekeeping gene and can be used to determine the expression level of the respective housekeeping gene.

In a preferred embodiment the agent binds specifically to the protein corresponding to a given marker or housekeeping gene. Preferably, this is a specific antibody to said protein. The antibody may be modified with a detectable label, for example by covalently attaching one or more fluorescent dyes to the antibody. The antibody may also be detectable by a labeled secondary antibody. Preferably, the diagnostic kit also comprises said labeled secondary antibody.

As mentioned above, the agent is an antibody which binds specifically to the protein corresponding to a given marker or housekeeping gene. The antibody may be a common antibody (which is composed of two heavy protein chains and two light chains), Fab fragments of a common antibody, single-chain variable fragments or single-domain antibody (sdAb). Said antibody specifically binds to the respective marker, which preferably has one of the amino acid sequences shown in SEQ ID NO: 14 to 23 (table 3); or to a housekeeping marker, which preferably has one of the amino acid sequences shown in SEQ ID NO: 24 to 26 (table 3). Further preferred, the respective antibody specifically recognizes an epitope (a stretch of 5 or more consecutive amino acid residues), within one of the amino acid sequences shown in SEQ ID NO: 14-26.

Regardless of structure, an antibody fragment binds with the same antigen that is recognized by the full-length antibody, and, in the context of the present invention, methods of making and screening antibody fragments are well-known in the art.

In another preferred embodiment the agent binds specifically to the mRNA or cDNA corresponding to a given marker. Preferably such an agent is an oligonucleotide primer set suitable for the specific amplification of a complete or partial sequence of the mRNA or cDNA corresponding to a given marker in a polymerase chain reaction. The oligonucleotide primer set may comprise two specific oligonucleotide primers that hybridize to the coding or untranslated region of the mRNA or cDNA. The oligonucleotide primer set may also only include one specific oligonucleotide primer that hybridizes to the coding or 5'-untranslated region or 3'-untranslated region of the mRNA or cDNA and a second unspecific oligonucleotide primer that hybridizes to the polyadenosine or polythymidine region of the mRNA or cDNA, respectively. Said oligonucleotide primers specifically bind to the respective mRNA or cDNA, which preferably has one of nucleotide sequences shown in SEQ ID NO: 1 to 10 (table 3); or to a housekeeping marker, which preferably has one of the nucleotide sequences shown in SEQ ID NO: 11 to 13 (table 3).

As used herein the term "polyadenosine region" means a portion at the 3'-end of the mRNA consisting of at least 10, 15, 20, 30, 50, 80, 100, 150, 200 or more consecutive adenosine residues.

As used herein the term "polythymidine region" means a portion of the cDNA, prepared from above mentioned mRNA, located at the 5'-end of the cDNA strand which is complementary to the mRNA from which the cDNA is prepared, and which portion consists of at least 10, 15, 20, 30, 50, 80, 100, 150, 200 or more consecutive thymidine residues.

Most preferably an oligonucleotide primer set comprises a forward primer with a length of 10 to 40 nucleotides that possesses at least 70% sequence identity with a continuous sequence of the same length selected from the DNA sequence of the respective marker and either a reverse primer with a length of 10 to 40 nucleotides that possesses at least 70% sequence identity with a continuous sequence of the same length selected from the sequence complementary to the DNA sequence of the respective marker, or a reverse primer with a length of 10 to 40 nucleotides that possesses at least 70% sequence identity with a continuous polyadenosine or polythymidine sequence of the same length. The DNA sequences for the individual markers and housekeeping genes are listed under SEQ NO ID: 1 to 13 (table 3). For the purpose of the present invention, each list sequence also comprises its reverse complement.

For the purpose of this invention, it is defined here that in order to determine the sequence identity of two nucleic acid sequences, the sequences are aligned for optimal comparison purposes. For the purpose of defining the oligonucleotide sequences mentioned above, the alignment should preferably not contain any gaps. The nucleotides at corresponding nucleotide positions are then compared. When a position in the first sequence is occupied by the same nucleotide as the corresponding position in the second sequence, then the molecules are identical at that position.

The sequence identity between the two sequences is given in percent and is a function of the number of identical positions shared by the sequences (i.e., % identity=number of identical positions/total number of positions (i.e. overlapping positions)*100). Preferably, the two sequences are the same length.

The skilled person will be aware of the fact that several different computer programmes are available to determine the homology between two sequences. For instance, a comparison of sequences and determination of percent identity between two sequences can be accomplished using a mathematical algorithm. In a preferred embodiment, the percent identity between two amino acid sequences is determined using the Needleman and Wunsch (J. Mol. Biol. (48): 444-453 (1970)) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

In yet another embodiment, the percent identity between two nucleotide sequences is determined using the GAP program in the GCG software package (available at http://www.gcg.com), using a NWSgapdna. CMP matrix and a gap weight of 40, 50, 60, 70, or 80 and a length weight of 1, 2, 3, 4, 5, or 6. In another embodiment, the percent identity between two nucleotide sequences is determined using the algorithm of B, Meyers and W. Miller (CABIOS, 4:11-17 (1989) which has been incorporated into the ALIGN program (version 2.0) using a PAM120 weight residue table, a gap length penalty of 12 and a gap penalty of 4.

MODES FOR CARRYING OUT THE PRESENT INVENTION

Figure 1:
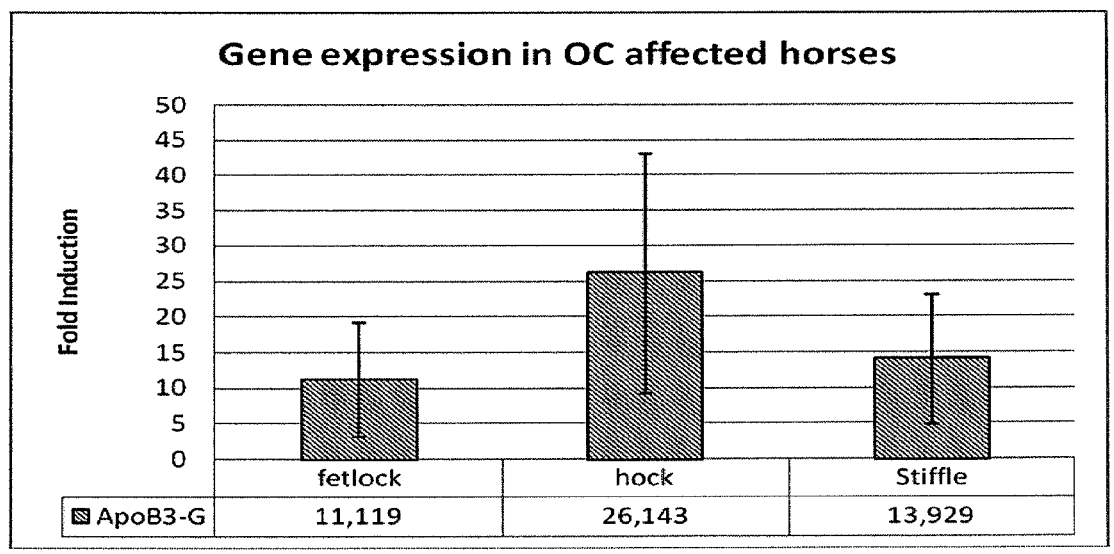
FIG. 1 shows the expression level of ApoB-3G in blood samples from horses affected by osteochondrosis in the fetlock joint, the stifle joint or the hock joint as compared to the control group.

In particular, the present invention provides an in vitro method or assay for the diagnosis of osteochondrosis or the prediction of the likelihood of its onset in a horse, comprising the steps
a) measuring the expression level of a marker in a sample obtained from said horse with an agent that can be used to determine the expression level of said marker, and
b) comparing the expression level measured in step a) to the expression level of said marker measured in a sample obtained from one or more horses not affected by osteochondrosis,
characterized in that the marker is ApoB-3G, wherein an increase in the expression level of ApoB-3G is indicative of osteochondrosis.

In a preferred embodiment the horse is not more than twelve months old.

In a preferred embodiment the present invention provides a method for the diagnosis and/or prediction of which joint in a horse (genus *Equus*, preferably *Equus caballus*) is or will be affected by osteochondrosis by additionally measuring the expression levels of the markers Dsh1, Foxl1, Hp, PPP2R1A-a, RUSC2 and WASH1. In this method, an increase in the expression level of each PPP2R1A-a and WASH1, a decrease in the expression level of each Dsh1, Foxl1, Hp and RUSC2 is indicative of affection of the fetlock joint;
a decrease in the expression level of each Dsh1, Hp, PPP2R1A-a, RUSC2 and WASH1 and no change in the expression level of Foxl1 is indicative of affection of the hock joint; and
a decrease in the expression level of each Dsh1, Foxl1, Hp, PPP2R1A-a, RUSC2 and WASH1 is indicative of affection of the stifle joint.

In a further preferred embodiment the present invention provides a method for the diagnosis and/or prediction of which joint in a horse (genus *Equus*, preferably *Equus caballus*) is or will be affected by osteochondrosis by additionally measuring the expression levels of the markers Dsh1, Foxl1, Hp, Mark2, PPP2R1A-a, WASH1, ISG17, PPP2R1A-b and RUSC2. In this method, an increase in the expression level of each PPP2R1A-a, PPP2R1A-b and WASH1, a decrease in the expression level of each Dsh1, Foxl1, Hp, Mark2 and RUSC2 and no change in the expression level of ISG17 is indicative of affection of the fetlock joint;
a decrease in the expression level of each Dsh1, Hp, ISG17, Mark2, PPP2R1A-a, PPP2R1A-b, RUSC2 and WASH1 and no change in the expression level of Foxl1 is indicative of affection of the hock joint; and
a decrease in the expression level of each Dsh1, Foxl1, Hp, ISG17, Mark2, PPP2R1A-a, PPP2R1A-b, RUSC2 and WASH1 is indicative of affection of the stifle joint.

In a preferred method the horse in not more than twelve months old.

The present invention also provides an in vitro method or assay for the prediction of the likelihood of the onset of osteochondrosis in a horse (genus *Equus*, preferably *Equus caballus*), comprising the steps
a) measuring the expression level of two or more markers in a sample obtained from said horse, and
b) comparing the expression level measured in step a) to the expression level of said marker measured in a sample obtained from one or more horses not affected by osteochondrosis,
characterized in that
at least one of the markers is ApoB-3G and the additional marker(s) is/are selected from the list consisting of Dsh1, Foxl1, Hp, ISG17, Mark2, PPP2R1A-a, PPP2R1A-b, RUSC2 and WASH1. In a preferred method the sample is a blood sample, which can be whole blood, blood serum or plasma. In a further preferred method of the present invention the horse is *Equus caballus*, and most preferred the horse is *Equus caballus* which is not more than 12 months old.

The present invention further provides an in vitro method or assay for the diagnosis of osteochondrosis or prediction of the likelihood of its onset in a horse (genus *Equus*, preferably *Equus caballus*), comprising the steps
a) measuring the expression level of a marker in a sample obtained from said horse with an agent that can be used to determine the expression level of said marker, and
b) comparing the expression level measured in step a) to the expression level of said marker measured in a sample obtained from one or more horses not affected by osteochondrosis;

wherein in step a) and b) the data of one or more or all of the following markers are obtained: Dsh1, Foxl1, Hp, PPP2R1A-a, RUSC2 and WASH1;

c) judging that the fetlock joint, the hock joint or the stifle joint is or will be affected by osteochondrosis from the data:

i) an increase in the expression level of each PPP2R1A-a and WASH1, a decrease in the expression level of each Dsh1, Foxl1, Hp and RUSC2 is indicative of affection of the fetlock joint;

ii) a decrease in the expression level of each Dsh1, Hp, PPP2R1A-a, RUSC2 and WASH1 and no change in the expression level of Foxl1 is indicative of affection of the hock joint; and iii) a decrease in the expression level of each Dsh1, Foxl1, Hp, PPP2R1A-a, RUSC2 and WASH1 is indicative of affection of the stifle joint.

In a preferred embodiment the expression level of ApoB-3G is measured, wherein an increase in the expression level of ApoB-3G is indicative of osteochondrosis.

According to a further preferred embodiment in step a) and b) the data of one or more or all of the following markers are obtained: Dsh1, Foxl1, Hp, Mark2, PPP2R1A-a, WASH1, ISG17, PPP2R1A-b and RUSC2; and step c) is as follows:

c) judging that the fetlock joint, the hock joint or the stifle joint is or will be affected by osteochondrosis from the data:

i) an increase in the expression level of each PPP2R1A-a, PPP2R1A-b and WASH1, a decrease in the expression level of each Dsh1, Foxl1, Hp, Mark2 and RUSC2 and no change in the expression level of ISG17 is indicative of affection of the fetlock joint;

ii) a decrease in the expression level of each Dsh1, Hp, ISG17, Mark2, PPP2R1A-a, PPP2R1A-b, RUSC2 and WASH1 and no change in the expression level of Foxl1 is indicative of affection of the hock joint; and iii) a decrease in the expression level of each Dsh1, Foxl1, Hp, ISG17, Mark2, PPP2R1A-a, PPP2R1A-b, RUSC2 and WASH1 is indicative of affection of the stifle joint.

The present invention will be explained in more detail in the following examples which are not limiting the scope of the present invention in any way.

Examples

Diagnosis of Osteochondrosis in Young Horses

28 Belgian Warmblood horses with osteochondrosis and 11 Belgian Warmblood horses free of osteochondrosis were included in this study. All horses were no more than 12 months old.

The horses were checked for osteochondrosis-specific lesions using radiography. All horses were sedated for the radiographic examination using detomidine (0.01 mg/kg IV) alone or combined with butorphanol (0.02 mg/kg IV). The following views were taken: dorso 60° proximo-palmaro-distal oblique and weight bearing lateromedial views of the front feet, lateromedial views of the 4 fetlocks, lateromedial and plantarolateral-dorsomedial oblique views of the hocks and a lateromedial view of the stifles. Horses with palmar or plantar fragmentations of the proximal phalanx were not included in this study. Horses were diagnosed on the basis of characteristic lesions of abnormal endochondral ossification located in the metacarpo and metarso-phalangeal (n=12), tibiotarsal (n=4), and femoro-patellar joints (n=12). Horses with multiple lesions were excluded from the study. Eleven horses without any evidence of osteochondrosis-specific lesions were analyzed as a control group.

Blood was collected from each horse using the PAXgene blood RNA kit (Qiagen, Courtaboeuf, France). The samples were frozen for later analysis.

For each sample, total RNA was extracted from 2.5 ml total blood using the PAXgene blood RNA kit (Qiagen, Courtaboeuf, France). The quality of total RNA extracted was checked by capillary electrophoresis analysis using an Agilent BioAnalyser 2100 (Agilent, Palo Alto, Calif., USA). RNA quantity was measured using a spectrophotometer NanoDrop ND-1000 (Thermo Scientific, Les Ulis, France).

cDNA was synthesized using 700 ng of total RNA per sample using the MMLV reverse transcription kit according to the manufacturer's protocol (Invitrogen, Carlsbad, Calif.).

Real-time PCR analysis was performed using a 7900HT ABI Prism Real-Time PCR System 384 wells. The reactions were set up using 1 µl of first cDNA, 3.33 µM of each primer and 2.5 µl of SYBR Green (Roche, Basel, Switzerland) in a 4 µl reaction volume. Cycling conditions were 40 cycles of 95° C. for 10 s, 57° C. for 20 s, and 72° C. for 30 s.

Real-time PCR analysis was performed for each of the markers and housekeeping genes listed in table 1. For each measured marker or housekeeping gene, a cycle threshold value (Ct-value) was obtained (see table 1).

The expression levels of the markers in horses affected by osteochondrosis and in the control group were compared by calculating $2^{-\Delta\Delta Ct}$ (Schmittgen and Livak, Nature Protocols, 3(6), pages 1101-1108 (2008)). Here, $\Delta Ct = Ct_{Marker} - Ct_{Housekeeping\ gene}$, and $\Delta\Delta Ct = \Delta Ct_{Subject} - \Delta Ct_{Control\ group}$. The results of this calculation is given in table 2, FIG. 1 and FIG. 2.

For comparison of the quantitative variables the normality was tested using Shapiro-Wilk, the normality was rejected and a non-parametrical method was used to assert of significant differential gene expression. A Kruskall-Wallis test and a Nemenyi test were used to identify the difference. All statistical tests were performed on the Delta Cycle Threshold (dCt) matrix and using R software v2.14.0. All tests performed were performed with 5% type I (alpha) error.

Figure 2:
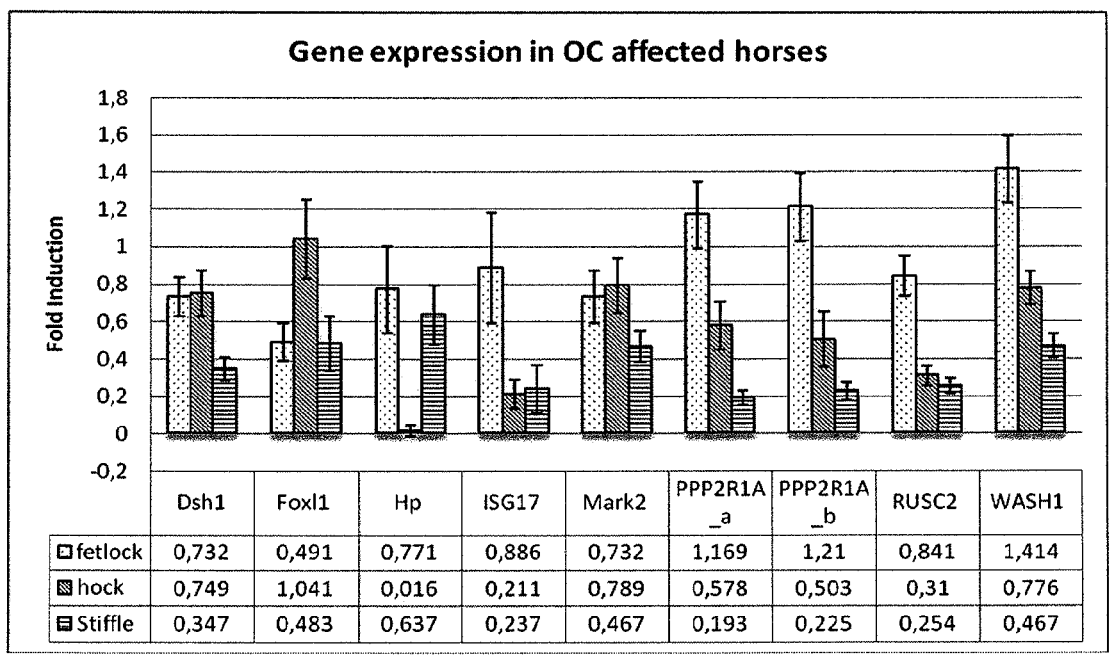
FIG. 2: The expression levels of selected markers in blood samples from horses affected by osteochondrosis in the fetlock joint, the stifle joint or the hock joint as compared to the control group.

The data in table 2, FIG. 1 and FIG. 2 demonstrate the expression levels of the markers ApoB-3G, Dsh1, Foxl1, Hp, ISG17, Mark2, PPP2R1A-a, PPP2R1A-b, RUSC2 and WASH1 are indicative of osteochondrosis in young (<12 months) horses. The data also show that the expression pattern of these markers is indicative of which joint is affected by osteochondrosis. ApoB-3G was found highly overexpressed in blood samples of horses affected by osteochondrosis, regardless of the affected joint (FIG. 1). Dsh1 was found underexpressed in blood samples of horses affected in the three joints, but especially in the stifle joint. The expression of Foxl1 is normal in horse affected in the hock joint, but this gene is found underexpressed in horses affected in the fetlock joint and the stifle joint. Hp is found underexpressed in fetlock joint and stifle joint affected horses, and is barely detectable in the hock joint affected horses. The expression of ISG17 is unchanged in fetlock joint-affected horses, but this gene is found underexpressed in hock joint and stifle joint-affected horses. The expression profile of Mark2 is basically the same than these of Dsh1/dvl1. PPP2R1A_a and _b share the same expression profile. They are overexpressed in fetlock joint-affected horses, but they were found underexpressed in hock joint and stifle joint affected horses. RUSC2 is slightly underexpressed in fetlock joint-affected horses, and is much more underexpressed in hock joint and stifle joint-affected horses. Finally, Wash1 is found overexpressed in blood samples of fetlock joint-affected horses, but was found underexpressed in hock joint and stifle joint-affected horses.

TABLE 1

Raw data of the real-time PCR analysis. For each subject, the age and the localization of the osteochondrosis-specific lesion is given ("1" indicates the fetlock joint, "2" the stifle joint, "3" the hock joint, and "4" indicates no lesion, i.e. control group). For each marker or housekeeping gene the measured Ct-value is given.

| Locali-zation | age (months) | \multicolumn{10}{c|}{markers} | \multicolumn{3}{c}{housekeeping genes} |
|---|---|---|---|---|---|---|---|---|---|---|---|---|---|---|
| | | RUSC | FoxI1 | ISG17 | PPP2R1A-b | PPP2R1A-a | Hp | ApoB-3G | WASH1 | Mark2 | Dsh1 | CtBP1 | Axin1 | CD44 |
| 1 | 10 | 20.7 | 19.5 | 18.3 | 15.1 | 15.1 | 9.6 | 17.7 | 17.6 | 16.0 | 20.3 | 10.7 | 14.0 | 10.8 |
| 1 | 6 | 20.0 | 20.2 | 17.0 | 14.9 | 14.7 | 20.3 | 10.8 | 17.3 | 15.3 | 18.8 | 10.3 | 13.1 | 10.1 |
| 1 | 7 | 21.4 | 19.6 | 16.5 | 16.0 | 15.6 | 11.2 | 17.6 | 17.9 | 16.4 | 19.6 | 11.5 | 14.2 | 11.2 |
| 1 | 8 | 21.1 | 21.3 | 16.1 | 15.7 | 15.6 | 9.6 | 11.8 | 17.1 | 15.6 | 19.6 | 10.8 | 13.9 | 10.9 |
| 1 | 7 | 21.1 | 21.6 | 17.5 | 15.4 | 15.1 | 21.2 | 8.2 | 17.0 | 16.1 | 19.8 | 10.7 | 13.9 | 9.7 |
| 1 | 6 | 20.9 | 20.0 | 15.3 | 15.5 | 15.5 | 10.0 | 6.8 | 16.8 | 15.4 | 19.5 | 10.7 | 13.6 | 10.9 |
| 1 | 6 | 19.7 | 20.9 | 17.0 | 14.1 | 14.0 | 9.9 | 8.8 | 16.2 | 15.0 | 18.6 | 9.8 | 12.9 | 9.8 |
| 1 | 10 | 21.4 | 19.1 | 15.6 | 15.0 | 14.9 | 21.4 | 7.8 | 17.5 | 15.8 | 19.3 | 10.5 | 13.7 | 10.4 |
| 1 | 11 | 20.7 | 19.8 | 18.2 | 15.1 | 15.0 | 20.7 | 10.1 | 17.1 | 15.7 | 19.6 | 10.5 | 13.9 | 10.1 |
| 1 | 6 | 21.9 | 19.6 | 18.5 | 15.1 | 15.0 | 9.6 | 17.2 | 17.7 | 15.6 | 18.8 | 10.4 | 13.7 | 10.1 |
| 1 | 4 | 23.1 | 19.9 | 17.1 | 16.3 | 16.2 | 21.9 | 8.6 | 18.7 | 16.4 | 21.6 | 11.7 | 14.8 | 11.4 |
| 1 | 11 | 20.0 | 18.9 | 16.7 | 14.8 | 14.6 | 9.8 | 15.4 | 16.9 | 15.2 | 19.1 | 10.4 | 13.2 | 10.3 |
| 2 | 11 | 25.5 | 19.6 | 18.5 | 19.8 | 21.3 | 11.6 | 9.6 | 19.8 | 17.5 | 20.9 | 11.7 | 14.5 | 11.0 |
| 2 | 11 | 23.0 | 21.9 | 21.7 | 18.3 | 18.7 | 11.9 | 10.6 | 18.9 | 17.0 | 20.2 | 11.2 | 14.1 | 11.0 |
| 2 | 4 | 24.4 | 20.4 | 16.5 | 17.0 | 16.8 | 11.4 | 16.9 | 18.7 | 16.6 | 22.5 | 11.3 | 14.6 | 11.1 |
| 2 | 5 | 23.2 | 20.7 | 22.7 | 18.2 | 18.2 | 11.6 | 11.0 | 19.6 | 17.0 | 21.8 | 10.9 | 14.1 | 10.9 |
| 2 | 5 | 21.2 | 18.4 | 19.8 | 16.8 | 15.8 | 9.0 | 18.4 | 16.8 | 14.3 | 18.2 | 9.2 | 12.2 | 8.6 |
| 2 | 8 | 25.4 | 22.3 | 16.9 | 18.6 | 18.8 | 21.7 | 13.4 | 20.7 | 17.2 | 22.7 | 11.8 | 15.4 | 11.8 |
| 2 | 7 | 22.3 | 20.0 | 17.1 | 17.1 | 16.9 | 10.8 | 7.4 | 18.0 | 15.9 | 20.0 | 10.8 | 13.8 | 10.5 |
| 2 | 6 | 25.7 | 21.9 | 22.5 | 19.0 | 18.9 | 11.2 | 14.0 | 19.8 | 17.1 | 21.1 | 11.0 | 14.6 | 10.9 |
| 2 | 11 | 21.9 | 21.1 | 19.4 | 17.4 | 17.3 | 10.4 | 9.4 | 19.4 | 17.0 | 21.3 | 11.7 | 15.0 | 11.6 |
| 2 | 1 | 25.9 | 19.1 | 21.9 | 18.7 | 18.7 | 21.7 | 10.0 | 20.0 | 17.1 | 21.4 | 12.3 | 15.5 | 11.2 |
| 2 | 12 | 26.5 | 22.7 | 20.7 | 18.9 | 18.6 | 21.2 | 12.7 | 19.5 | 17.1 | 21.9 | 11.9 | 15.0 | 10.9 |
| 2 | 6 | 23.3 | 20.2 | 19.4 | 16.6 | 16.6 | 11.8 | 8.8 | 19.1 | 16.4 | 22.1 | 11.4 | 14.2 | 10.9 |
| 3 | 10 | 21.5 | 19.3 | 19.1 | 15.8 | 15.9 | 21.9 | 10.3 | 17.7 | 16.2 | 19.6 | 10.6 | 13.8 | 10.5 |
| 3 | 6 | 23.3 | 19.3 | 20.1 | 18.2 | 17.9 | 11.8 | 14.1 | 18.6 | 15.9 | 20.1 | 11.7 | 14.7 | 11.5 |
| 3 | 10 | 22.7 | 19.0 | 18.9 | 16.6 | 16.4 | 9.6 | 8.2 | 18.7 | 16.0 | 20.0 | 11.1 | 14.4 | 10.5 |
| 3 | 11 | 23.5 | 21.3 | 21.1 | 17.3 | 16.9 | 21.7 | 9.2 | 18.6 | 16.8 | 21.5 | 11.5 | 14.3 | 11.0 |
| 4 | 9 | 21.4 | 20.0 | 18.2 | 16.6 | 16.4 | 21.1 | 9.2 | 18.5 | 16.8 | 20.1 | 11.6 | 14.6 | 11.6 |
| 4 | 5 | 20.7 | 18.0 | 16.2 | 14.8 | 14.8 | 9.7 | 18.0 | 18.6 | 15.5 | 19.6 | 10.5 | 14.0 | 10.3 |
| 4 | 5 | 21.7 | 17.9 | 19.1 | 16.5 | 16.1 | 9.8 | 16.7 | 18.1 | 15.7 | 20.0 | 11.6 | 14.7 | 10.9 |
| 4 | 4 | 19.9 | 19.2 | 12.9 | 14.7 | 14.4 | 10.7 | 16.2 | 16.1 | 15.0 | 19.5 | 10.1 | 13.3 | 10.8 |
| 4 | 5 | 22.6 | 21.0 | 13.9 | 16.4 | 16.4 | 23.0 | 15.6 | 18.7 | 16.6 | 20.3 | 11.8 | 14.7 | 11.8 |
| 4 | 7 | 23.8 | 18.4 | 21.4 | 18.2 | 18.2 | 22.6 | 12.5 | 20.1 | 17.7 | 19.2 | 13.2 | 16.0 | 12.3 |
| 4 | 9 | 21.1 | 20.5 | 17.0 | 15.0 | 15.1 | 10.1 | 10.9 | 18.0 | 15.6 | 18.7 | 10.7 | 14.1 | 10.3 |
| 4 | 8 | 21.4 | 19.6 | 18.9 | 15.6 | 15.5 | 10.7 | 18.9 | 17.8 | 15.9 | 19.8 | 11.0 | 14.2 | 10.9 |
| 4 | 8 | 21.6 | 19.3 | 17.9 | 16.0 | 15.9 | 11.7 | 13.5 | 18.5 | 16.5 | 20.4 | 11.5 | 14.6 | 11.7 |
| 4 | 10 | 24.9 | 20.4 | 20.7 | 20.7 | a | a | a | a | a | a | a | a | a |
| 4 | 5 | 29.8 | — | 22.8 | 23.2 | a | a | a | a | a | a | a | a | a |
| 4 | 7 | 21.0 | 19.8 | 16.8 | 16.0 | 15.9 | 11.0 | 11.9 | 16.2 | 13.8 | 19.2 | 10.4 | 14.3 | 10.0 |

TABLE 2

Expression of markers in horses affected by osteochondrosis as compared to the control group. An arbitrary value of 1 is given to the expression level in the control group.

| | Fetlock | Hock | Stifle | Fetlock | Hock | Stifle |
|---|---|---|---|---|---|---|
| | \multicolumn{3}{c|}{Mean} | \multicolumn{3}{c}{Standard Deviation} |
| ApoB-3G | 11.119 | 26.143 | 13.929 | 7.958 | 16.878 | 9.085 |
| Dsh1 | 0.732 | 0.749 | 0.347 | 0.105 | 0.12 | 0.064 |
| FoxI1 | 0.491 | 1.041 | 0.483 | 0.101 | 0.209 | 0.143 |
| Hp | 0.771 | 0.016 | 0.637 | 0.23 | 0.028 | 0.158 |
| ISG17 | 0.886 | 0.211 | 0.237 | 0.296 | 0.078 | 0.128 |
| Mark2 | 0.732 | 0.789 | 0.467 | 0.138 | 0.146 | 0.084 |
| PPP2R1A-a | 1.169 | 0.578 | 0.193 | 0.177 | 0.126 | 0.04 |
| PPP2R1A-b | 1.21 | 0.503 | 0.225 | 0.182 | 0.149 | 0.049 |
| RUSC2 | 0.841 | 0.31 | 0.254 | 0.108 | 0.053 | 0.044 |
| WASH1 | 1.414 | 0.776 | 0.467 | 0.182 | 0.089 | 0.066 |

TABLE 3

List of markers/housekeeping genes and corresponding SEQ ID NOs.

| marker/housekeeping gene | nucleotide sequence SEQ ID NO. | amino acid sequence SEQ ID NO. |
|---|---|---|
| ApoB-3G | 1 | 14 |
| Dsh1 | 2 | 15 |
| FoxI1 | 3 | 16 |
| Hp | 4 | 17 |
| ISG17 | 5 | 18 |
| Mark2 | 6 | 19 |
| PPP2R1A-a | 7 | 20 |
| PPP2R1A-b | 8 | 21 |
| RUSC2 | 9 | 22 |
| WASH1 | 10 | 23 |
| Axin1 | 11 | 24 |
| CtBP1 | 12 | 25 |
| CD44 | 13 | 26 |

The invention claimed is:

1. An in vitro method or assay for the diagnosis of osteochondrosis or prediction of the likelihood of its onset in a terrestrian mammal, comprising the steps
   a) obtaining a sample from a horse, which is not more than 12 months old,
   b) measuring the expression level of a marker in the sample with an agent that can be used to determine the expression level of said marker, and
   c) comparing the expression level measured in step b) to the expression level of said marker measured in a sample obtained from one or more terrestrian mammals of the same species not affected by osteochondrosis, characterized in that
   the marker is ApoB-3G,
   wherein an increase in the expression level of ApoB-3G is indicative of osteochondrosis, and
   wherein ApoB-3G is cDNA synthesized using RNA extracted from the sample.

2. The in vitro method or assay according to claim 1, characterized in that the expression levels of one or more additional markers are measured, wherein the additional markers are selected from the list consisting of
   Dsh1, wherein a decrease in the expression level of Dsh1 is indicative of osteochondrosis;
   Foxl1, wherein a decrease in the expression level of Foxl1 is indicative of osteochondrosis;
   Hp, wherein a decrease in the expression level of Hp is indicative of osteochondrosis;
   ISG17, wherein a decrease in the expression level of ISO 17 is indicative of osteochondrosis;
   Mark2, wherein a decrease in the expression level of Mark2 is indicative of osteochondrosis;
   PPP2R1A-a, wherein an increase or decrease in the expression level of PPP2R1A-a is indicative of osteochondrosis;
   PPP2R1A-b, wherein an increase or decrease in the expression level of PPP2R1A-b is indicative of osteochondrosis;
   RUSC2, wherein a decrease in the expression level of RUSC2 is indicative of osteochondrosis; and
   WASH1, wherein an increase or decrease in the expression level of WASH1 is indicative of osteochondrosis.

3. The in vitro method or assay according to claim 2, characterized in that the expression levels of the additional markers Dsh1, Foxl1, Hp, PPP2R1A-a, RUSC2 and WASH1 are measured.

4. The in vitro method or assay according to claim 2, characterized in that the expression levels of all of the additional markers are measured.

5. The in vitro method or assay according to claim 1, characterized in that the expression levels of at least one, two, several or all of the additional markers Dsh1, Foxl1, Hp, PPP2R1A-a, RUSC2 and WASH1 are measured, wherein the expression levels of Dsh1, Foxl1, Hp, PPP2R1A-a, RUSC2 and WASH I are further used to diagnose and/or predict whether the fetlock joint, the hock joint or the stifle joint is or will be affected by osteochondrosis.

6. The in vitro method or assay according to claim 1, characterized in that the expression levels of at least one, two, several or all of the additional markers Dsh1, Foxl1, Hp, PPP2R1A-a, RUSC2 and WASH1 are measured, wherein an increase in the expression level of each PPP2R1A-a and WASH1, a decrease in the expression level of each Dsh1, Foxl1, Hp and RUSC2 is indicative of affection of the fetlock joint; a decrease in the expression level of each Dsh1, Hp, PPP2R1A-a, RUSC2 and WASH1 and no change in the expression level of Foxl1 is indicative of affection of the hock joint; and a decrease in the expression level of each Dsh1, Foxl1, Hp, PPP2R1A-a, RUSC2 and WASH1 is indicative of affection of the stifle joint.

7. The in vitro method or assay according to claim 5, characterized in that the expression levels of at least the markers of one of the following marker combinations are measured: Foxl1 and WASH1; or Foxl1 and PPP2R1A-a.

8. The in vitro method or assay according to claim 1, characterized in that the expression levels of at least one, two, several or all of the additional markers Dsh1, Foxl1, Hp, Mark2, PPP2R1A-a, WASH1, ISG17, PPP2R1A b and RUSC2 are measured, wherein the expression levels of Dsh1, Foxl1, Hp, Mark2, PPP2R1A-a, WASH1, 15017, PPP2R1A-b and RUSC2 are further used to diagnose and/or predict whether the fetlock joint, the hock joint or the stifle joint is or will be affected by osteochondrosis.

9. The in vitro method or assay according to claim 1, characterized in that the expression levels of at least one, two, several or all of the additional markers Dsh1, Foxl1, Hp, Mark2, PPP2R1A-a, WASH1, ISG17, PPP2R1A-b and RUSC2 are measured, wherein
   an increase in the expression level of each PPP2R1A-a, PPP2R1A-b and WASH1, a decrease in the expression level of each Dsh1, Foxl1, Hp, Mark2 and RUSC2 and no change in the expression level of ISG17 is indicative of affection of the fetlock joint;
   a decrease in the expression level of each Dsh1, Foxl1, Hp, ISG17, Mark2, PPP2R1A-a, PPP2R1A-b, RUSC2 and WASH1 and no change in the expression level of Foxl1 is indicative of affection of the hock joint; and
   a decrease in the expression level of each Dsh1, Foxl1, Hp, ISG17, Mark2, PPP2R1A-a, PPP2R1A-b, RUSC2 and WASH1 is indicative of affection of the stifle joint.

10. The in vitro method or assay according to claim 8, characterized in that the expression levels of at least the markers of one of the following marker combinations are measured: Foxl1 and WASH1; or Foxl1 and PPP2R1A-a; or Foxl1 and PPP2R1A-b.

11. The in vitro method according to claim 1 characterized in that the expression levels of the markers are determined by measuring the mRNA of the corresponding marker.

12. The in vitro method according to claim 1 characterized in that the samples are blood samples.

13. The in vitro method according to claim 1, wherein the agent is an oligonucleotide primer set comprising a forward primer with a length of 10 to 40 nucleotides that possess at least 70% sequence identity with a continuous sequence of the same length selected from the DNA sequence of ApoB-3G and either a reverse primer with a length of 10 to 40 nucleotides that possess at least 70% sequence identity with a continuous sequence of the same length selected from the sequence complementary to the DNA sequence of ApoB-3G or a reverse primer with a length of 10 to 40 nucleotides that possess at least 70% sequence identity with a continuous polyadenosine or polythymidine sequence of the same length.

14. An in vitro method or assay for the detection of a marker in a terrestrian mammal, comprising the steps
   a) obtaining a sample from a horse, which is not more than 12 months old, and
   b) measuring the expression level of the marker in the sample with an agent that can be used to determine the expression level of said marker,
   characterized in that
   the marker is ApoB-3G,
   wherein an increase in the expression level of ApoB-3G is indicative of osteochondrosis, and wherein ApoB-3G is cDNA synthesized using RNA extracted from the sample.

15. The in vitro method or assay according to claim 14, characterized in that the expression levels of one or more additional markers are measured,
   wherein the additional markers are selected from the list consisting of
   Dsh1, wherein a decrease in the expression level of Dsh1 is indicative of osteochondrosis;
   Foxl1, wherein a decrease in the expression level of Foxl1 is indicative of osteochondrosis;
   Hp, wherein a decrease in the expression level of Hp is indicative of osteochondrosis;
   ISG17, wherein a decrease in the expression level of ISG17 is indicative of osteochondrosis;
   Mark2, wherein a decrease in the expression level of Mark2 is indicative of osteochondrosis;
   PPP2R1A-a, wherein an increase or decrease in the expression level of PPP2R1A-a is indicative of osteochondrosis;
   PPP2R1A-b, wherein an increase or decrease in the expression level of PPP2R1A-b is indicative of osteochondrosis;
   RUSC2, wherein a decrease in the expression level of RUSC2 is indicative of osteochondrosis; and
   WASH1, wherein an increase or decrease in the expression level of WASH1 is indicative of osteochondrosis.

16. The in vitro method or assay according to claim 15, characterized in that the expression levels of the additional markers Dsh1, Foxl1, Up, PPP2R1A-a, RUSC2 and WASH1 are measured.

* * * * *

SEQUENCE LISTING

<160> NUMBER OF SEQ ID NOS: 26

<210> SEQ ID NO 1
<211> LENGTH: 666
<212> TYPE: DNA
<213> ORGANISM: Equus caballus

<400> SEQUENCE: 1

| | | | | | |
|---|---|---|---|---|---|
| atggaggcca | gtgcagcacc | catggccagg | cgcctcatgg | acgaagacac | cttcactgag | 60 |
| aacttcaaga | atgtgaactg | gccacgcaag | acctacctgt | gctatgaggt | ggagctcccg | 120 |
| gatggagact | ccagggtccc | cccaggctgg | acaagggct | tcctgcgcaa | caagcctatt | 180 |
| cacatgcccg | ggccacccg | cgacgcagag | atgcgcttcc | tggacctgat | ctcttcttgg | 240 |
| aagctggacc | agaaactgcg | ctacagggtc | acctgtttca | tctcctggag | ccctgcgct | 300 |
| gactgtgctc | agagattggc | tgggttcctg | cgggagaaca | gccacgtgag | cctgcgcatc | 360 |
| ttcgcttccc | gcatctttac | caaggagac | tacaaggcgg | gactgcgcac | cctacaggcg | 420 |
| gctgaggccc | aaatcgccat | catggcctca | gaagagtttg | agcactgctg | gaagaccttc | 480 |
| gtggacaacc | agggaaggac | cttccaggcc | tgggatgagc | tggatgctga | gagtcgctac | 540 |
| tggtccatgg | agctgcagcg | cattctacag | ccgactgctc | ctccctccct | gcctcccctc | 600 |
| tactttcctc | cctcccatcc | tgtccctggc | ccttcctttc | actcactcag | aggctcctct | 660 |
| gggtga | | | | | | 666 |

<210> SEQ ID NO 2
<211> LENGTH: 1992
<212> TYPE: DNA
<213> ORGANISM: Equus caballus
<220> FEATURE:
<221> NAME/KEY: misc_feature
<222> LOCATION: (1)..(1)
<223> OTHER INFORMATION: n is a, c, g, or t

<400> SEQUENCE: 2

| | | | | | |
|---|---|---|---|---|---|
| ncggagtcca | agatcatttc | tcacatggtc | gaggaggaga | cgccgtacct | ggtcaagctg | 60 |
| cgcgtagcgg | ccgagcgcgt | cacgctggcc | gacttcaaga | acgtgctcag | caaccggccc | 120 |
| gtgcacgcct | acaaattctt | cttcaagtcc | atggaccagg | acttcggggt | ggtgaaggag | 180 |
| gagatctccg | atgataatgc | caagctgcct | tgtttcaacg | gccgtgtggt | ctcctggctc | 240 |
| gtgctggccg | agggcgcaca | ctcagacgca | gggtctcagg | gcactgacgg | tcacgcagac | 300 |
| ctgccccgc | ctcttgagcg | acaggcggc | atcggggact | cccggccccc | ctccttccac | 360 |
| ccaaatgtgg | ccagcagccg | tgatgggatg | acaacgaga | ccagcacaga | gtccatggtc | 420 |
| agccaccggc | gggagcgagt | ccgacgccgg | aaccgtgaag | aggccacccg | gaccaacggg | 480 |
| caccttaggg | gggaccggcg | gcgggaccta | gggctgcccc | ctgacagcac | gtccactgtg | 540 |
| ctgagcagtg | aactcgagtc | cagcagcttc | atcgactcag | acgaggatga | caacacaagt | 600 |
| cggctgagca | gctccacgga | gcagagcacc | tcctcccggc | tcatccggaa | gcacaagcgc | 660 |
| cggcggcgga | agcagcgcat | gcggcagacg | gaccgtgcct | cctccttcag | cagcatcaca | 720 |
| gactccacta | tgtccctgaa | tatcatcacc | gtcacgctca | acatggagag | gcaccacttc | 780 |
| ttgggcatca | gcattgtggg | ccagagcaac | gaccgggcg | acgcgggcat | ctacctccgc | 840 |
| ctccataagg | gcggagctgt | ggcccgccga | tgcccgcca | tcgagcctgg | tgacatgctg | 900 |
| cttgcaggtg | cgagggttgc | aagggagcta | gctgaggggc | ccgagctgac | ccagtcgccc | 960 |
| atcgacccag | ccgcctgggt | gtcccacaca | gcggcgctga | ctggagccct | gccccgctac | 1020 |

-continued

```
ggtacgagcc cctgctccag cgccgtctcg cgcaccagct cctcctcact aaccagctct    1080
gtgcccggcg ctgcacagct ggaagaggcg ccactgaccg tgaagagtga catgggcgcc    1140
atcgttcggg tcatgcagct gccagactca ggcctggaga tccgcgaccg tatgtggctc    1200
aagatcacca tcgccaacgc cgtcatcggg gcggatgtgg tggactggct gtacacacac    1260
gtggagggct tcaaggagcg gcgggaggcg cggaagtacg ccagcagcat gctgaagcgt    1320
ggtttcctgc ggcacaccgt gaacaagatc accttctccg agcagtgcta ctacgtcttc    1380
ggggacctgt gcagcaatct cgcggccctg aacctcaaca gtggctccag tggggcctca    1440
gagcaggaca cgctgccccc gctgcccccac ccggccgctc cctggcccct gggtcagggt    1500 taccccctacc agtacccagg ccccccgccc tgcttcccgc ccgcatacca ggaccccagc    1560
ttcagctacg gcagcggcag tgctgggagt cagcagagtg aaggaagcaa aagcagtggg    1620
tccacccgga gcgccggcgg gagcagccgg cgggcactgg gccgagaaaa ggagcaccgg    1680
gcggctggag ctgggggcag cggcagcgag tcggatcaca cagcaccaag tggggtgggt    1740
ggcagtggct ggcgggagcg tccggctagc cagctcagct gtggcagcag cccacgcagc    1800
caggcctcgg ccgctgcccc ggggctcccc ccactgcacc ccctgacgaa ggcctactcg    1860
gtagtgggtg gccgcctgg ggggccgcct gttcgggagc tggctgctgt ccccccagag    1920
ctgacaggca gccgccagtc tttccagaag gccatgggga accctgtga gttcttcgtt    1980 gacatcatgt ga                                                        1992
```

<210> SEQ ID NO 3
<211> LENGTH: 534
<212> TYPE: DNA
<213> ORGANISM: Equus caballus

<400> SEQUENCE: 3

```
gttgcctgcg tcgcggagag cgcagcgccg gcgcccactc gccatgagcc acctcttcag     60
tccccggctg cctgctctgg ccgcctcgcc catgctttat ctgtacggcc ccgagagacc    120
cgggctgcct ctggccttcg cccccgcggc cgctttggcc gcctcgggcc gggcggagcc    180 ccccccagaag ccgccctaca gctacatcgc gctcatagcc atggcgatcc aggacgcgcc    240
ggagcagagg gtcacgctca acggcatcta ccagttcatc atggaccgct tccccttcta    300
ccacgacaac cggcagggct ggcagaacag catccgccac aacctttcgc tcaacgactg    360
cttcgtcaag gtgccccgcg agaaagggcg accgggcaag ggcagctact ggacgctgga    420
ccctcgctgt ctggatatgt tcgagaacgg caactaccgg cgccggaaga ggaagcccaa    480
gccgggaccc ggggacgggg aggccaagcg agcccgcgta gagacgcagg agcg          534
```

<210> SEQ ID NO 4
<211> LENGTH: 1074
<212> TYPE: DNA
<213> ORGANISM: Equus caballus

<400> SEQUENCE: 4

```
agcgccctgg gagccgttgt cgccctcctg ctctgggggc agcttttcgc tgtggacact     60
ggcaatgagg ccacagattt cacagatgac agctgcccaa agccccccga gattccgaat    120
ggctacgtgg agcacttggt tcgctatcag tgtaagaatt actacagact gcgcagtgaa    180
ggagatggag tgtatgcctt aaacagcgag aagcagtggg taaataaggc cagcggaacg    240
aaacttcctg aatgtgaagc agtgtgtgga aagcccaaga tccagtggga tcaggtgcaa    300
```

| | |
|---|---|
| cggattatag gtggattgct ggacgccaaa ggcagctttc cctggcaggc taagctggtg | 360 |
| tcccgccaca acctcaccac aggggccaca ctgatcagtg aacaatggct gctgaccacg | 420 |
| gctcagaatc tcttcctgaa tcatacacct gatgcaaaac caaagacat tgcccctact | 480 |
| ttaaaactct atgtggggag aaagcagcct gtggagattg agaaggtggt cttccacccg | 540 |
| gactatcagg aggtagacat cgggctcatc aagctcaaag agaaggtgcc cgttggtgag | 600 |
| agagtcatgc ccatctgcct accttcaaaa gattatgcgc aagtggggcg tgtgggttat | 660 |
| gtgtctggct gggggcgaaa tgccaacttt aatttcacgg agctactgaa gtacgtcacg | 720 |
| ctgccggtgg ctgaccaaga cacctgtgtg aagcactacg aaggcagcac tgtgcccgaa | 780 |
| aagaagacaa acaggagctc tgtcggcgtg cagcccatcc tgaatgaaca ccttctgt | 840 |
| gctggcctgt ccaagtttca ggaggacacc tgctacggcg atgctggcag tgcctttgtc | 900 |
| attcacgatg aggaggacga cacctggtac gcggctggga tcctgagctt tgataagagc | 960 |
| tgtgctgtgg ccgagtatgg agtgtacgtg aaggtgccct ccatcctgga ttgggttcag | 1020 |
| aaaactatcg ctgagaacta atgcaaggct ggcggccagc actgcctgag agca | 1074 |

<210> SEQ ID NO 5
<211> LENGTH: 465
<212> TYPE: DNA
<213> ORGANISM: Equus caballus

<400> SEQUENCE: 5

| | |
|---|---|
| ggtggggagc tgaaggtgaa gatgctgggg ggtgaattcc tggtgcccct gaaggactcc | 60 |
| atgctggtgt cggagctgaa gcagcagatc gcccagaaga caggagtgcc cccctcccag | 120 |
| cagcgcctgg ccacccaccc agccggcatg gtgctgcagg acagggtccc cctcgtcagc | 180 |
| cagggcctgg gacccggcag cacggtcgtg cttgtcgtgc agaactgtga caccccctg | 240 |
| agcatcctgg tgaggaacgg gaagggccgc agcagtgcct atgaggtccg gctgacgcag | 300 |
| acggtggcag agctcaagca gcaggtgtgc ctgcgggaga gcgtgcaggc cgaccagttc | 360 |
| tggctgactt tcgaggggaa gcccatggac gaccagctcc acctggggga atacgagctt | 420 |
| acagccgggt gcacagtgta catgaacttg cgcctgcggg gggc | 465 |

<210> SEQ ID NO 6
<211> LENGTH: 2684
<212> TYPE: DNA
<213> ORGANISM: Equus caballus

<400> SEQUENCE: 6

| | |
|---|---|
| gctgaacgag agggacacgg agcagcccac cttgggacat cttgactcca agcccagcag | 60 |
| taagtccaac atgctgcggg gccgcaactc agccacctct gctgacgagc agccccatat | 120 |
| tggcaactat cgactcctca agaccattgg caagggtaac ttcgctaagg tgaagctggc | 180 |
| tcggcacatc ctaactggga agaggtagc tgtgaagatc attgacaaga ctcagttgaa | 240 |
| ctcctccagc ctccagaaac tcttccggga agtaagaata tgaaggtttt gaatcaccc | 300 |
| caacatagtt aaattatttg aagtgatcga aactgaaaaa actctctacc ttgtcatgga | 360 |
| gtacgccagt ggaggagagg tgtttgacta cctagtggct catggcagga tgaaagaaaa | 420 |
| agaggctcga gccaaattcc gccagatagt gtctgctgtg cagtactgtc accagaagtt | 480 |
| tattgttcat agagacctaa aggcagaaaa cctgcttttg gatgctgata tgaacatcaa | 540 |
| gattgcagac tttggcttca gcaacgagtt caccttgggg aacaagctgg acaccttctg | 600 |
| tggcagccct ccttatgccg ccccggagct cttccagggc aaaaagtacg atggccccga | 660 |

```
ggtggacgtg tggagcctgg gtgttatcct gtatacactg gtcagcggat ccctgccttt      720
tgacggacag aacctcaagg agctgcggga gcgggtactg aggggaaaat accgtattcc      780
gttctacatg tccacggact gtgaaaacct gcttaagaaa tttctcattc tcaatcccag      840
caagagaggc actttagagc aaatcatgaa agatcgatgg atgaacgtgg gtcacgaaga      900
tgatgaatta aagccttatg tggagccact ccctgactac aaggacccc ggcggacaga       960 gttgatggtg tccatgggtt acacacggga agagatccag gactcgctgg tgggccagag     1020
gtacaacgag gtgatggcca cctatctgct cctgggctac aagagctccg agctggaggg     1080
cgacaccatc accttgaagc cccggcctcc agctgatctg accaatagca gcgcccttc      1140 cccctcccac aaggtacagc gcagcgtctc agccaacccc aagcagcggc gcttcagtga     1200
ccaggctggt cctgccattc ccacctcgaa ttcctactct aagaagactc agagtaacaa     1260
cgcagaaaat aagcggccgg aggaggaccg ggagtcaggg cggaaggcca gcagcacagc     1320
caaagtgcct gccagccccc tgccggcct ggagaggaag aagaccaccc ccaccccctc       1380
cacgaacagt gtcctctcca ccagcacaaa tcgaagcagg aattccccac ttttggagag     1440
ggccagcctt ggccaggcct ccatccagaa tggcaaagac agcctaacca tgccagggtc     1500
ccgggcctcc acggcttctg cttccgccgc agtctctgcg gcccggcccc gccagcacca     1560
gaaatccatg tcggcctccg tgcacccaa caaggccact gggctgcccc ccacggacag      1620
taactgtgag gtgccgcggc ccaggcaagt cacagccccc cagcgtgtcc ctgtcgcctc     1680
cccctccgcc cacaacatca gcagcagtgg tggagcccca gaccgaacta atttccccg      1740 gggtgtgtcc agtcgaagca ccttccacgc tgggcagctc cggcaggtgc gggaccagca    1800
gaatttgccc tacggtgtga ccccagcctc tccctcgggc aacagccagg ccggcggggg    1860
cgcctctggg agcatcttca gcaaattcac ctccaagttt gtacgcagaa atctgtcttt    1920
caggtttgcc agaaggaacc tgaatgaacc tgaaagcaaa gaccgagtgg agacgctcag     1980
acctcacgta gtgggcagcg gaggtaatga caaagaaaag gaggagtttc gggaggccaa     2040
gccccgctcc ctgcgcttca cgtggagtat gaagaccacg agctccatgg agccgaacga     2100
gatgatgcgg gagatccgca aggtgctgga cgcaaacagc tgccagagcg agctgcacga     2160
gaagtacatg ctgctgtgca tgcacggcac gccgggccac gagaacttcg tgcagtggga     2220
gatggaggtg tgcaaactgc cgcggctctc tctcaacggt gttcgattta gcggatatc     2280 gggcacctcc atggccttca aaaacattgc ctccaaaata gccaacgagc tgaagcttta     2340
acaggctgcc aggagtgggg ggccacggag gcgggccagc tggacttcgc tgctggggcc     2400
ggccgctccg ccccacctgg gcgagactgc agagatggat cggtgtgtct ccccctgctg     2460
gcacatctcc cctccccgcc cttctcagtt ttttcttcca tgtttgtggg ggatgggaga     2520
tggctctttc ccccccacat ttaccctgc ccagaagtcc cccttccc ccctcgctcc        2580 cacaggaggc aaaggaaggg gagggagggt ggggggcag ggctccccct cggtactgcg      2640
gttgcacaga gtatttcgcc taaaccaaga aatttttaa tacc                       2684
```

<210> SEQ ID NO 7
<211> LENGTH: 2218
<212> TYPE: DNA
<213> ORGANISM: Equus caballus

<400> SEQUENCE: 7

```
cctgtaaagt ggctcgggcg cccccacgcc cgcctttcct cccctcagcc ctgcccctcc       60
```

| | |
|---|---|
| ccatcccggt ttcagcacgg cgctggccgc agtctgacag gaacggacgg agccaagatg | 120 |
| gcggcggccg acggcgatga ctcgctctac cccatcgcgg tgctcataga cgagctccgc | 180 |
| aacgaggatg tccagcttcg cctcaacagc atcaagaagc tgtccaccat cgccttggcc | 240 |
| ctcggggtgg aaaggacccg cagtgagctt ctgcccttcc ttacagacac catctacgat | 300 |
| gaggacgagg tcctcttggc cctggcggaa cagctgggaa ccttcaccac tctcgtggga | 360 |
| ggccccgagt acgtgcactg cctgctgcca cccctggagt cactggccac agtggaggag | 420 |
| acagtggtgc gggacaaggc agtggagtcc ttgcgggcca tctcgcacga gcactcaccc | 480 |
| tccgacctcg aggcccactt cgtgccgcta gtgaagcggc tggcgggcgg cgactggttc | 540 |
| acctcccgta cctcagcctg cggcctcttc tccgtctgct acccccgcgt gtccagtgct | 600 |
| gtcaaggcgg aacttcgaca gtactttcgg aacctgtgct cagatgacac ccctatggtg | 660 |
| cggcgggccg cagcctccaa gctggggggag ttcgccaagg tgctggagct ggacaacgtc | 720 |
| aagagtgaga tcatccccat gttctccaac ctggcctctg acgagcagga ctcggtgcgg | 780 |
| ctgctggctg tggaggcgtg cgtgaacatt gcccagctcc tgcccagga ggatctggag | 840 |
| gccctagtga tgcccaccct gcgccaggct gctgaggaca gtcgtggcg tgtgcgatac | 900 |
| atggtggccg acaagttcac agagctccag aaagcagtgg ggcctgagat caccaagacg | 960 |
| gacctggttc ccgccttcca gaacctgatg aaagactgtg aggccgaggt gagggccgca | 1020 |
| gcctcccaca aggtcaaaga attctgtgaa atctgtcag ctgactgtcg ggagaatgta | 1080 |
| atcatgaccc agattttgcc ctgcatcaag gagctggtgt cggatgccaa ccaacacgtc | 1140 |
| aagtcagctc tggcctccgt cattatgggc ctctctccca tcctgggcaa agacaacacc | 1200 |
| attgagcacc tcctgccccct cttcctggct cagctaaagg atgagtgccc agaagtgcgg | 1260 |
| ctgaacatca tctccaacct ggactgtgta aatgaggtga tcggcatccg gcagctgtcc | 1320 |
| cagtccctgc tccccgccat cgtggagctg gctgaggatg ccaagtggag agtgcggctg | 1380 |
| gccatcattg agtacatgcc cctgctggct ggacagctgg gggtagagtt ctttgatgag | 1440 |
| aaactcaact ccttgtgcat ggcctggctc gtggatcacg tatatgctat ccgtgaggcg | 1500 |
| gccaccagca acctgaaaaa gctggtggag aagtttggca aggagtgggc ccatgccacc | 1560 |
| atcatcccta aggtcttggc catgtctggg gaccccaact acctgcaccg catgactaca | 1620 |
| ctcttctgca tcaatgtgct atctgaggtt tgtgggcagg acatcaccac caagcacatg | 1680 |
| ctgcccacgg tcctgcgtat ggctggggac cccgttgcca acgtccgctt caacgtggcc | 1740 |
| aagtccctcc agaagatagg acccatcctg acaacagca cactccagag tgaagtcaag | 1800 |
| cccatcctag agaagctgac ccaggaccag gatgtagatg tcaagtactt tgcccaggag | 1860 |
| gctctgactg ttctgtctct cgcctgatgc tggaagagga gccaatgccg gcctctggtg | 1920 |
| tccttccacc ccaattccct ccctcaggga gacagtgggg ggcctttggc tgtcactccc | 1980 |
| tgtgcatggt ctgacccccat gcccttccc ccagcacggt tctttctctt cccagcctgg | 2040 |
| gaatccgact tctcactgtc cacctcccaa ggggctgggg gagcacaagg tgggacaggg | 2100 |
| cagtgaccct gggaggaagg ggccactcct gcccacgtcg ggggagagat gtgagcgtcc | 2160 |
| caggtcactg gctcctgctg ctgtaatggg gaccccctcc cccattgact tctccacc | 2218 |

<210> SEQ ID NO 8
<211> LENGTH: 2218
<212> TYPE: DNA
<213> ORGANISM: Equus caballus

<400> SEQUENCE: 8

```
cctgtaaagt ggctcgggcg ccccccacgcc cgcctttcct cccctcagcc ctgcccctcc      60
ccatcccggt ttcagcacgg cgctggccgc agtctgacag gaacggacgg agccaagatg     120
gcggcggccg acgcgatga ctcgctctac cccatcgcgg tgctcataga cgagctccgc     180 aacgaggat tccagcttcg cctcaacagc atcaagaagc tgtccaccat cgccttggcc     240
ctcggggtgg aaaggacccg cagtgagctt ctgcccttcc ttacagacac catctacgat     300
gaggacgagg tcctcttggc cctggcgaaa cagctgggaa ccttcaccac tctcgtggga     360
ggccccgagt acgtgcactg cctgctgcca ccctggagt cactggccac agtggaggag     420
acagtggtgc gggacaaggc agtggagtcc ttgcggccca tctcgcacga gcactcaccc     480
tccgacctcg aggcccactt cgtgccgcta gtgaagcggc tggcgggcgg cgactggttc     540
acctcccgta cctcagcctg cggcctcttc tccgtctgct accccgcgt gtccagtgct     600 gtcaaggcgg aacttcgaca gtactttcgg aacctgtgct cagatgacac ccctatggtg     660
cggcgggccg cagcctccaa gctggggggag ttcgccaagg tgctggagct ggacaacgtc     720
aagagtgaga tcatccccat gttctccaac ctggcctctg acgagcagga ctcggtgcgg     780
ctgctggctg tggaggcgtg cgtgaacatt gcccagctcc tgcccagga ggatctggag     840 gccctagtga tgcccacccct gcgccaggct gctgaggaca agtcgtggcg tgtgcgatac     900
atggtggccg acaagttcac agagctccag aaagcagtgg ggcctgagat caccaagacg     960
gacctggttc ccgccttcca gaacctgatg aaagactgtg aggccgaggt gagggccgca    1020
gcctcccaca aggtcaaaga attctgtgaa aatctgtcag ctgactgtcg ggagaatgta    1080
atcatgaccc agattttgcc ctgcatcaag gagctggtgt cggatgccaa ccaacacgtc    1140
aagtcagctc tggcctccgt cattatgggc ctctctccca tcctgggcaa agacaacacc    1200
attgagcacc tcctgcccct cttcctggct cagctaaagg atgagtgccc agaagtgcgg    1260
ctgaacatca tctccaacct ggactgtgta aatgaggtga tcggcatccg gcagctgtcc    1320
cagtccctgc tccccgccat cgtggagctg gctgaggatg ccaagtggag agtgcggctg    1380
gccatcattg agtacatgcc cctgctggct ggacagctgg gggtagagtt ctttgatgag    1440
aaactcaact ccttgtgcat ggcctggctc gtggatcacg tatatgctat ccgtgaggcg    1500
gccaccagca acctgaaaaa gctggtggag aagtttggca aggagtgggc ccatgccacc    1560
atcatcccta aggtcttggc catgtctggg acccccaact acctgcaccg catgactaca    1620
ctcttctgca tcaatgtgct atctgaggtt tgtgggcagg acatcaccac caagcacatg    1680
ctgcccacgg tcctgcgtat ggctggggac cccgttgcca acgtccgctt caacgtggcc    1740
aagtccctcc agaagatagg acccatcctg gacaacagca cactccagag tgaagtcaag    1800
cccatcctag agaagctgac ccaggaccag gatgtagatg tcaagtactt tgcccaggag    1860
gctctgactg tttctgtctct cgcctgatgc tggaagagga gccaatgccg gcctctggtg    1920
tccttccacc ccaattccct ccctcaggga gacagtgggg ggcctttggc tgtcactccc    1980
tgtgcatggt ctgaccccat gccccttccc ccagcacggt tctttctctt cccagcctgg    2040
gaatccgact tctcactgtc cacctcccaa ggggctgggg gagcacaagg tgggacaggg    2100
cagtgaccct gggaggaagg ggccactcct gcccacgtcg ggggagagat gtgagcgtcc    2160
caggtcactg gctcctgctg ctgtaatggg accccctcc cccattgact tctccacc      2218
```

<210> SEQ ID NO 9
<211> LENGTH: 5027
<212> TYPE: DNA

<213> ORGANISM: Equus caballus

<400> SEQUENCE: 9

```
atgcccttgt tcgaactttc agaatggat agtcccccaa agctgactgg agagaccctc      60
atcgtccacc acatccccct ggtgcactgt caagtcccag acaggcagtg ccgtggaggg     120
gcaagtggag gtagtgggag cacaagaccc aatccattct gcccatcgga gctgggcatc    180
accaagcctg atcaagacct aggacaagct gactccctgc tctacaatag tcggcactct    240
tctacagggg gatctgcacg gtctgcagac agcaccaaga gtagggtcg ggatggaaga     300
ggccctgggg cccctaaacg acacaatccc ttcttgcagc aggagggtgt ggctgagcca    360
ggatttggtg acctatatga ggacagcatt ggtgatagtg ccacccagca gcagtcattc    420
cacctgcatg gggctggcca gcccaccttc cagctatcct cttccagct gccaccaact    480
ggccccagag tgggcaggcc atgggcaca agacgtagtc gggctggagt ggtggagggg    540
caagaacagc agccagtaac caccttggat acccaggagt gcagcactag ctactgctgc    600
cggccagagc tggaagcaga gaccatgaag ctggatgagt gtggggacc tggtgggagt    660
ggcagtgggg gtggagccag tgatacctct ggcttttcct ttgaccagga atggaagctg    720
agttcagatg aatccccaag gaaccccgga tgcacaggct caggaccca gcactgccgc    780
tgcagtagca catccagtca gtccgagacg gctgaccagt ccatgggcta tgtgagtgac    840
tcgtcctgca acagctcaga tggcgtgctt gtcactttca gcaccctcta caacaagatg    900
catggcaact cccatgccaa tctcaactca gccccgcaat cttgcagcga ctcttccttc    960
tgcagccatt cagaccctgg cgccttctac ctggacctgc aaaccttccc tgctgaggag   1020
tcccaccacc ctaacaatgg aggaagggaa ggaggctatg gttgtcctca tgcctcatct    1080
cctgagcttg atgccaactg caactcctac cacccacatt gtgagccctg ccagctgtg    1140
gctgacctca cagcctgctt ccagagccag gcccgtcttg ttgtggccac acagaattac   1200
tataaacttg tcacctgtga cctgtcctcc aatcatccc caagcccagc tggctcttcc    1260
attactagct gctctgagga acacaccaag ataagtcctg caccaggccc tggcccacac    1320
cctggcccta gccagccctc tgagtattac ctattccaga agccagaagt gcagccagag    1380
gaacaagaag caggggttc ctcagaggaa gcagcagctc ccgtgggccc tgctatgatc    1440
gagggccaag tgtacaccaa tacttcaccc cccaaccta gcactggacg tcagcgctct    1500
cgaagctatg atcgcagcct cgaacgaagc cctcctgttc gcctgggctc actggaacgc    1560
atgttgagtt gccagtgcg cctgagtgag ggccctgcag ccctggctgg gcctagctcc    1620
ccacctaggc gggtcaccct cttgctgag cttgccaagg gccggaagaa agctgcaggc    1680
tctggctccc caccacttcg agtgagcatt ggagactcct cccaggattt ctctcctatc   1740
caagaaaccc aacaagatag ggtgggcccc ctggataagg gcactcgctg tagccatagc    1800
ctaccaccaa tgccattggg gccaggcatg gacctacttg acccagagcc ctggtccacc    1860
caggtctgtc agggccccca gtcaagtgag atgccatctg ctggcctcag agctgctgag    1920
caaggcccc tggcccagct gatggatcca gggcctgctc tcccagggag cccagccaac    1980
agccatcctc agagggatgc aagagccaga gcggatgggg tggtgctga gagccgacca    2040
gtccttcgct acagcaagga gcagaggcca acaacgctgc ccatccagcc tttcgtgttc    2100
cagcaccact tccccaagca gttggccaag gccgggccc tccacagcct ttcccaactc    2160
tacagcctct cgggctgcag ccgtgcacag cagcctgccc cactggctgc ccccactgct    2220
caagtcccag ccccagctcc ttcaggggag tcacaagcat ccgccaacaa agggccggg     2280
```

```
aaagctgggc ctgagccaga aacctcacgg ccatcacccc tgggcagcta ctcccccatt    2340
cggagtgctg gcccctttgg gcccagcacc gactcttctc cttccacttc gtgctcccct    2400
cccctagagc aggccacagc cacagaaagc ccacccccat ggagccactc ctgtcctcct    2460
gctgtccggc ctgccacctc ccagcagcca ccaaaggagg atcagaagat actgaccttg    2520
gctgagtacc gactccatgg aacaggaagc ctgcctcctc tgggctcctg gagatctggc    2580
ttcagccgag cagagagcct ggccggggga ggtggtgagg cagcatggc ctccaggccc    2640 agtaacgcca accacctatc ccctcaagca ctcaagtggc gggagtacag gaggaagaac    2700
ccactagggc cgcctggctt gtcagggagc ctagaccgaa ggccacagga agctcggctg    2760
gcccgaagga accccatctt tgagtttcct ggctccctca gtgctgctgg ccatctgaac    2820
tgccggctga atggtcaagt agtgaagcca ttaccactga cctgccctga cttccaagac    2880 ccctttcct tgaccgagaa gcctccagct gagttttgtc tatccccaga tggcaactca    2940
gaggccattt ccattgacct gcttcagaaa aagggctcg tgaaagctgt taacactgct    3000
gtggacctca ttgtggccca ttttggcaca agccgggatc tggggtgaa ggcaaagctt    3060 gggaatagtt ctgtgagccc caatgtaggc cacctggttc tgaagtactt gtgccctgcc    3120
gtccgggctg tgctggagga tgggctcaag gcctttgtgc tagatgtcat cattgggcaa    3180
cggaagaaca tgccgtggag tgtggttgag gcttccacac agctaggccc atccaccaag    3240
gtcctgcatg gcctctacaa caaagtcagc caattcccag agctcaccag tcataccatg    3300
cgcttcaacg ccttcatcct cggcctgctc aacatccggt ccctggagtt ctggtttaat    3360
cacctctata accacgaaga tatcatccag acccactacc agccatgggg cttcctgagc    3420
gcagcacata ccgtgtgccc cggcctcttt gaggagctgc tgctgctgct acagcccctg    3480
gccctgctgc ccttcagcct cgacttgctc ttccagcacc ggctgctgca aagtgggcag    3540
cagcagcggc agcacaagga gctgctgcgg gtgtcccagg acctgctgct atccgcccac    3600
tcaacgctgc agttggccca ggcccggggc caggagggcc ctggagacat ggacagggca    3660
gcccatgggg agcgggtgaa gggtgtgggt gccccagaag gtggagaaga tgaagaggaa    3720
gaagaagaga cagaagagat ggcagaggca gctgggggct cagggcgtgg caggtgggcc    3780
caaggtgggc aggctggctg gtggtaccag ctcatgcaga gctcccaggt ctacatcgat    3840
ggctccactg agggttctag gtttccccga ggtggcagca atagcagcag tggcagcagc    3900
agtgagaaaa agaaaggagc cggaggcagg gggccacccc ccgggagg agtcgtggag    3960 ggagctgagg cctgccctgc ccctgaggag actctgggca gggcctggcc cttctggatg    4020
ggaagccccc ctgattctgt gctggccgag ctgagacgca gtcgggagag ggaggggtcg    4080
actgctcccc cagcagaaaa tgaggaagga acctctgagc cttcacctgg ggcatcaag    4140 tggggacacc tttttgggtc ccgaaaggtt cagcgggaag cccgacccac aaacaggcta    4200
ccctcagact ggctgagcct ggacaagtcc atgttccaac tagtggtgca gacagtgggt    4260
gcccgccggg agccagagcc cagggagagc ctgcaggagc cacaccctcc agccctgccc    4320
tccaagcctc catgcaaggt gaaggcactg tgccaccatc tggccacagg ccctggacag    4380
ctgagcttcc acaagggaga catcctacgg gtgctgggc cagccaaagg agactggctg    4440
cattgcagcc gtggcactga catgggcctg gtgcctctgg cctacgtgac gttgaccccca    4500 actccaagtc caacgcccgg aagcagccaa aactgaggcc ctgtgcatgc tggtggcctc    4560
ggggacccct ataacccca gactcagagc ctgagagccc ttccctctgg cttggctact    4620
```

```
gagagtagac tgagagctgg gggccacata tgcctgtgct cagtattaat tactccccct    4680
taattgtccc agtgacctcg tccagatctc cacccaggaa aggagggaag ggacacagca    4740
ctgggctgcc aggatttccc cagcccatct gggccagccc ttccatgggt acagacaagt    4800
acatctgtat ggagggaggt gaccagaagc ccatttgcag ggttccctag gccaggtggt    4860
gaggaggagg ggtaacagta ttggggccag atccctaagc ccccagctgt aaataggctg    4920
tggccagtac ctggtgatca gaagagggag gaggagccca ggcttctgtt tatgtatttt    4980
atttatttat ttattacacc tattaataaa aaaggtgctc agcctcc                  5027

<210> SEQ ID NO 10
<211> LENGTH: 1740
<212> TYPE: DNA
<213> ORGANISM: Equus caballus

<400> SEQUENCE: 10
catgactccc acgaggaccc agcactcatt ggcagggcag acctacatgg tgcccctcat      60
ccagccggac ctgcggcgag aggaggccat ccagcaggtg gcagatgccc tgcagtacct     120
acagaaggtc tccggagaca tctttagcag gatctcccag cgagtagagc tcagccggag     180
ccagctgcag gccattgggg agagggtctc tttggcccag gccaagattg agaagatcaa     240
gggcagcaag aaggccatca aggtgttctc cagtgccaag tacccagctc agagcgcct     300 acaggagtat gggtccatct tcacaggggc ccaagaccct ggcctgcaga gacgcccccg     360
ctacaggatc cagagcaagc accgccccct ggatgagcgg gcctgcagg agaagctgaa     420 atacttccct gtgtgtgtga acacgaagct ggagcctgag gatgaggctg aggagggact     480
cgggggtctt cccagcaaca tcagctccgt cagctcctta ctgctcttca acaccactga     540
gaacctgtac aaaaaatatg tcttcctgga ccccctggct ggagctgtaa caaagaccca     600
tgtgatgctg ggggcagaga cggaagagaa gctgtttgat gcccctttgt ccatcagcaa     660
gagagagcag ctggagcaac aggttccaga gaactacttt tacgtgcccg acctgggcca     720
agtgcctgag atcgatgtcc atcctacct gcctgacctg ccaggcatcg ctgatgacct     780
catgtacagt gccgacctgg gcctggcat tgccccctct gcccctggta ccattccaga     840
gctgcccacc ttccacacag aggttgccga gcctttcaag ccagaccgag aagatggggt     900
gctaatagca ccccaccgc cacccccacc gccaccgcct cctccagccc cagcagtgct     960
ggtcagcgca ccccaccc cacccccacc cctgagcacg gcctctccgg gccaaggtac    1020
gagggaggat gagagcagag gtggtgtccg tccctcagtc ccggaagctc ccagggaagt    1080
ggttgagccc tccagtggcc gggccactct gctggagtct atccgccagg ctgggggcat    1140
tgccaaggcc aagctccgca gtgtcaagga gcgcaagctg gagaagaaga acagaagga    1200 acaggaacaa gtgagagcaa cgggccaagg tggggacctg atggcagatc tctttaacaa    1260
gctggtcatg aggcgcaaag gtatctccgg gaaaggaccg gcgcccgggg ccagcgaagg    1320
gccaggtgga gcctttgccc gaatgtcaga ctccatcccg cctctgcctc ccccacagca    1380
gccaccggga gaggaggacg aggatgactg ggaatcctag gcctcagctg ctgcttcctc    1440
cccagaactc aggcttagct atgggcctca cgccgaaaca gcgggatggg ctcctcggcc    1500
ggcagctctc agtccctgct gcccttggag ggaccgggat gtggaggact gtcccaagac    1560
tgtgcctgga ccttcttcag gaagcgggga ggccggcttc cgaggccaca cgctggaagg    1620
ggccgggggg agcccttgct ctctgcctgt gctctaccca ccccctcacc agcatgctct    1680
cttctctaaa gagacgctga gataaacaat ccatgaatca ataaagaagc ataacgcaag    1740
```

<210> SEQ ID NO 11
<211> LENGTH: 2667
<212> TYPE: DNA
<213> ORGANISM: Equus caballus

<400> SEQUENCE: 11

```
ctgtccgttg agcctcccct gagcgcattg ggcgaggccg tgccgcgcct ctccgggagc      60
cgggtccccg ggcccccccc cgcgcggcgg gacagattga ttcactttgg agccgtaagt     120
actgatgtat tagggtgcag ccctcgttgt tcattgacgc agagcccccaa aatgagtgtc    180
caagagcagg gtttcccctt ggacctcgga gcaagtttca ccgaagatgc cccccggccc     240
ccagtgcctg gtgaggaggg tgaactggtg tccacagacc ccaggcccgt cagccacagc     300
ttctgctccg ggaaaggccc cgggatcaaa ggtgagacat caacagccac tccgaggcgc     360
tcggatctgg acctggggta cgagcccgag ggcagcgcct ccccaccccc ccgtacttg      420
aagtgggccg agtcactgca ctccttgcta gacgatcaag atgggataaa cctgtttagg     480
actttcctga agcaggagga ctgtgctgac ctgctggact tctggtttgc ctgcagcggc     540
ttcaggaagc tggagccctg tgactcgaat gaggaaaaga ggctgaagct ggccaaagct     600
atttaccgaa agtacatcct tgataacaat ggcatcgtgt ccaggcaaac caagccagcc     660
accaagagct tcataaagga ctgcatcatg aagcagctga tcgatcctgc catgttcgac     720
caggcccaga cggaaatcca gtccaccatg gaggagaaca cctacccgtc cttcctcaag     780
tccgatattt atttggagta cacgaggaca ggctcagaga gcccgaagct ctgtagcgac     840
cagagctctg gtcagggac agggaagggc atacctggat acctgcccac tttgaatgaa     900
gacgaggagt ggaaatgtga ccaagatgta gatgaagacg atggcagaga ccctggtccc     960
cctggcaggc tcacgcagaa gctgctgctg agacggctg ccccgcgggc ctccgcaagt    1020
agacggtaca gcaaggcag agaattcagg tatggatcct ggcggagcc tgtcaacccc     1080
tactatgtca actccggcta cgccctcgcc ccagccacca gcgccaacga cagcgagcag    1140
cagagcctgt ccagcgatgc cgacagcctg tccctcaccg acagcagcgt ggatggagtc    1200
cctccgtaca ggatccgcaa gcagcaccgc cgggagatgc aggagagcgt ccaggtcaat    1260
gggcgggtgc ctctacctca cattccccgc acttaccgaa tgccaaagga gatccgcgtg    1320
gagccgcaga agtttgccgc ggagctcatc caccgcctgg aggccatcca gcggacgcgg    1380
gaggctgagg agaagctgga ggagcggctg aagcgcgtcc ggatggagga agaaggtgag    1440
gacgggcgacg tgtcctgtgg ccccccagga gccagtcaca agctgccttc tgccccagcc    1500
tggcaccact ccccgcccc ctatgcggac atgggctgca ccgggctgcg ggatgcgcac    1560
gaggagaacc ccgagagcat cctggacgag cacgtcagc gggtcatgag acgcctggc    1620
tgccagtccc cggggcccgg ccaccgttcc cctgacagcg tacacgtgcc caaggtgcca   1680
ggggtgctgg ggggcatagc tcccgggcac ggtaagcacg cactcaagtc gggggcgaag    1740
ctggacgccg ccggcctgca tctccacagg cacagccacc accatggcca ccacggcttg    1800
gccaggccca aagagcaggc cgaggccgag gctgccgcc gggtccagag cagcttctcg    1860
tgggccctgg agcagcatgg ccacacgcc aaaccccgca gccactccga gagtgtgggc    1920
gctgccccata tcaccagcga cggcctgacc tacagcggga aggcgggcac cacctgcaaa    1980
agaaacacca gaaggccga gtcagggaag agcatggggg ccgaggcacc aggcccctca   2040
gaggacgcgg agaagaacca gaagatcatg cagtggatca tcgaggggga gaaggagatc   2100
```

```
agcaggcaca ggaaggcggg ccacggatct tccgggacaa agaagcagca ggggcatgag    2160
agctccaggc ccctgtccat cgagcgtccg ggggccgtgc acccctgggt cagcgctcag    2220
ctccggaact ccgtccagcc ctctcatctc ttcattcaag accctaccat gccgcccaac    2280
ccagccccca accctctgac ccagctggag gaggcccgca ggcgcctgga ggaggaagag    2340
aagagagcca gcaagctccc ctcgaagcag aggatgaagt cgcagaggaa ggtgggcagt    2400
agcagcaccc agccgtgtga cagcatcgtt gtggcctact acttctgtgg ggagcccatc    2460
ccctaccgga ccctggtgag aggccgcgcc gtcaccctgg ccagttcaa ggagctgctg     2520 accaagaagg gcaactacag atactacttc aagaaagtga gcgatgagtt cgactgtggg    2580
gtggtgtttg aggaggttcg cgaggatgag gccgtcctgc ccgtcttcga ggagaagatc    2640
atcggcaagg tggagaaggt ggactga                                       2667

<210> SEQ ID NO 12
<211> LENGTH: 1336
<212> TYPE: DNA
<213> ORGANISM: Equus caballus

<400> SEQUENCE: 12
cctgtcgttg caggcgtccg acctccgatc atgaacgggc ccatgcaccc ccggcccctg      60
gtggcgctgc tcgatggccg ggactgtacg gtcgagatgc ccatcctgaa ggacgtggcc    120
acggtggcct tctgtgatgc gcagtccaca caggagatcc acgagaaggt gctgaacgag    180
gccgtgggcg cgctcatgta ccacaccatc acgctgacga gggaggacct ggagaagttc    240
aaagccctcc gaataatcgt gcggatcggc agcggctttg acaacatcga catcaagtcg    300 gcggggact  taggcatcgc tgtctgcaac gtgccggcgg cgtccgtgga ggagactgca    360
gactccacca tgtgccacat cctcaacctc taccgaagaa ccacctggct gcaccaggca    420
ctgcgagagg gcacccgagt gcagagcgtc gagcagatcc gcgaagtggc ttccggagcc    480
gcgaggatcc gtggggagac cttgggcatc attgggctag tcgcgtgggg gcaggcggtg    540
gccctgcggg ccaaggcatt cggcttcaac gtgctcttct acgaccccta cctgtcggac    600
ggcacggagc gggcgctggg gctgcagcgg gtcagcaccc tgcaggacct gctcttccac    660
agtgactgcg tgaccctgca ctgcggcctc aatgagcaca ccaccaccct catcaacgac    720
ttcaccgtca gcagatgag acaaggggcc ttcctggtga acacggcccg gggcggcctg    780
gtggacgaga aggccttggc ccaggcccta aggaggggc ggatacgtgg cgcggccctg    840
gacgtgcacg agtcggagcc cttcagcttc agccagggtc ctctgaagga cgcacccaac    900
ctgatctgca ccccccacgc agcctggtac agcgagcagg cgtccatcga gatgcgcgag    960
gaggcagccc gggagatccg gagagccatc acaggccgga tccccgacag cctgaagaac   1020
tgcgtcaaca aggaccacct gacagctgcc acccactggg ccagcatgga cccagccgtc   1080
gtgcaccccg agctcaacgg ggccgcctac aggtaccccc cgggcgtggt gggtgtggcc   1140
cccagtggca tcccagcagc tgtcgaaggc attgtcccca cgccatgtc cctgtcccac    1200 ggcctgcccc ccgtgtccca cccgcccac gccccttctc ccggccaaac cgtgaagccc    1260
gaggcggata gagaccaccc gagtgaccag ttgtagcccg ggcggagctc tgcagcctca   1320
gtcggcgggg ccgccg                                                  1336

<210> SEQ ID NO 13
<211> LENGTH: 2297
<212> TYPE: DNA
<213> ORGANISM: Equus caballus
```

<400> SEQUENCE: 13

```
cgggaccccc agctccactg gctcggcttc gccgtcgctc ccacaccatg gacaagtttt    60
ggtggcgcgc agcctgggga ctctgcctcg tgccgctgag cctggcgcag atcgatttga   120
acataacctg ccgatacgca ggggtattcc atgtggagaa aaatggccgc tacagcatct   180
cgcggacgga ggccgcggac ctgtgcaagg cttctcaacag caccctgccc accatggccc   240
agatgcagaa agcgctgaac attggctttg agacctgcag gtacgggttc atagaagggc   300
acgtggtcat cccccggatc caccccaact ccatctgtgc cgccaacaac acgggcgtgt   360
acatcctcac gtccaacacc tctcagtacg acacctattg cttcaatgcc tcagctccgc   420
ccgaagaaga ctgtacctcg gtcacagacc tgcccaacgc cttcgaggga cccattacca   480
taactatcgt taaccgtgat ggcactcgct acaccaagaa aggcgagtac agaactaacc   540
ctgaagacat caaccccagc accccctgcgg atgacgacgt gagcagtggg tcctccagcg   600
aaagaagcac ttcaggaggc tacagcatct tccacaccca ccttccaacc actcgcccca   660
cccaagacca gagcagtccc tgggtgtctg acagcccaga gaagactccc actaccagta   720
cggattcaaa tgtcatctca gcaggctggg agccacctga agaaaacgaa gatgaaagag   780
acaaacaccc cagttattct ggatcaggca ttgatgatga tgaagatttt gtctccagca   840
ccattccaac caaaccacgg attttttaagt cccagaagt gaacgaggat tggcggcaat   900
ggagcccagg ccattcaact ccaggcatct tacttcagac agccacaagg atgactgatg   960
tggacagaag tggcaccagt gcttatggag aaagtcagac ccaggaacca cattctcctc  1020
tcgttcacca tgagcatcat gacgaagagg agacccagca ttctacaagc tcaacctggg  1080
cgcttttctag taggacagca gaagacacag ctacccagaa agagcagtgg tttgaggacg  1140
gatggcgtgg ggaatacacc caaacgccaa aggaagactc tccttcagca acagggacag  1200
ctgtcacaac agcctcagcc cacgacagcc atccaaatcg aagaatgaca acgcagagtc  1260
aagaggacag ttcctggact tatttcttcg acccaatctc acatccaaag ggacgaggtc  1320
atcacacgga aagatggatg gatgtggact ccagccgtag tacaacgctt cagccttctg  1380
cagatccaag cacaggtttg gtggaagagt tggacaggac aagacctctt tcaatgacaa  1440
ctcagcagag tcatactcag agcttctcta cgtcacatgg aggcttggaa gaagataaag  1500
accatccaat gacttctact ccatcatcta gcaataggaa tgatggcaga ggtggaagaa  1560
gaagtggaaa cttttctgaa gactcagcta cttcaggaga gggctatact gctcatgccc  1620
cagacacaaa ggaatacaac accctcaccc cagtgacccc tgctaagact gggtccccag  1680
gagttactga agttattgtt cttgacgatt ctaactctca tgttgatggt tccttttcag  1740
gtaatttggc cacttaccga gcctctggcg ggagggccca gaccaccccac ggatctgaaa  1800
caagtggaca ctcgactggg agtcaagaag gtggggcaag cacaacctcg ggtcccatac  1860
ggagacctca aattccagaa tggctgatca tcttggcgtc cctcctggcc ctggctctga  1920
ttctcgcagt ttgcattgct gtcaacagtc gaagaaggtg tggacagaag aagaagctgg  1980
tgatcaacaa tggcaatgga gctgtggacg acagaaaggc aagtgggctc aatggagagg  2040
ccagcaggtc tcaggagatg gtgcacttgg tgaacaagga gtcgtcagag acccaagacc  2100
agtttatgac agccgacgag acacggaacc tgcagaatgt ggacatgaag attggggtgt  2160
agcacctgca ccttgacctt gggaagaaac cacagtcaga gagagcagtc acaggggct  2220
gggacatttc acagatgtga tgtgctactg actgcttcat tcgggatctt ttttttaacat  2280
``` aaaatttct actcctt                                                                               2297

<210> SEQ ID NO 14
<211> LENGTH: 284
<212> TYPE: PRT
<213> ORGANISM: Equus caballus

<400> SEQUENCE: 14

Met Glu Ala Arg Arg Leu Met Asp Glu Asp Thr Phe Thr Glu Asn Phe
1               5                   10                  15

Lys Asn Val Asn Trp Pro Arg Lys Thr Tyr Leu Cys Tyr Glu Val Glu
            20                  25                  30

Leu Pro Asp Gly Asp Ser Arg Val Pro Pro Gly Trp Asp Lys Gly Phe
        35                  40                  45

Leu Arg Asn Lys Pro Ile His Met Pro Gly Pro Pro Arg Asp Ala Glu
    50                  55                  60

Met Arg Phe Leu Asp Leu Ile Ser Ser Trp Lys Leu Asp Gln Lys Leu
65                  70                  75                  80

Arg Tyr Arg Val Thr Cys Phe Ile Ser Trp Ser Pro Cys Ala Asp Cys
                85                  90                  95

Ala Gln Arg Leu Ala Gly Phe Leu Arg Glu Asn Ser His Val Ser Leu
            100                 105                 110

Arg Ile Phe Ala Ser Arg Ile Phe Thr Lys Gly Asp Tyr Lys Ala Gly
        115                 120                 125

Leu Arg Thr Leu Gln Ala Ala Glu Ala Gln Ile Ala Ile Met Ala Ser
    130                 135                 140

Glu Glu Phe Glu His Cys Trp Lys Thr Phe Val Asp Asn Gln Gly Arg
145                 150                 155                 160

Thr Phe Gln Ala Trp Asp Glu Leu Asp Ala Glu Ser Arg Tyr Trp Ser
                165                 170                 175

Met Glu Leu Gln Arg Ile Leu Gln Pro Thr Glu Ala Leu Val Leu Val
            180                 185                 190

Trp Arg Asp Pro Gly Val Ala Ile Trp Glu Leu His Leu Ile Ala Gln
        195                 200                 205

Arg Thr Trp Pro Thr Cys Leu His Val Arg Asp Val Ser Ser Ala Leu
    210                 215                 220

Ser Asp Gln Phe Met Gly Gly Ser Glu Asn Pro Cys Pro Met Lys Thr
225                 230                 235                 240

Arg Gly Asp Val Thr Cys Ser Asn Val Phe Thr Phe Leu Gln Arg Ser
                245                 250                 255

Pro Pro Ile His Pro His Thr Leu Asp Pro Asp Ser Leu Trp Gln Gln
            260                 265                 270

Arg Pro Ser Asp Glu Cys Ser Leu Leu Arg Ser Pro
        275                 280

<210> SEQ ID NO 15
<211> LENGTH: 663
<212> TYPE: PRT
<213> ORGANISM: Equus caballus
<220> FEATURE:
<221> NAME/KEY: misc_feature
<222> LOCATION: (1)..(1)
<223> OTHER INFORMATION: Xaa can be any naturally occurring amino acid

<400> SEQUENCE: 15

Xaa Glu Ser Lys Ile Ile Ser His Met Val Glu Glu Glu Thr Pro Tyr
1               5                   10                  15

```
Leu Val Lys Leu Arg Val Ala Ala Glu Arg Val Thr Leu Ala Asp Phe
            20                  25                  30

Lys Asn Val Leu Ser Asn Arg Pro Val His Ala Tyr Lys Phe Phe Phe
        35                  40                  45

Lys Ser Met Asp Gln Asp Phe Gly Val Lys Glu Glu Ile Ser Asp
50                      55                  60

Asp Asn Ala Lys Leu Pro Cys Phe Asn Gly Arg Val Val Ser Trp Leu
65                  70                  75                  80

Val Leu Ala Glu Gly Ala His Ser Asp Ala Gly Ser Gln Gly Thr Asp
                85                  90                  95

Gly His Ala Asp Leu Pro Pro Leu Glu Arg Thr Gly Gly Ile Gly
                100                 105                 110

Asp Ser Arg Pro Pro Ser Phe His Pro Asn Val Ala Ser Ser Arg Asp
            115                 120                 125

Gly Met Asp Asn Glu Thr Ser Thr Glu Ser Met Val Ser His Arg Arg
        130                 135                 140

Glu Arg Val Arg Arg Asn Arg Glu Glu Ala Thr Arg Thr Asn Gly
145                 150                 155                 160

His Leu Arg Gly Asp Arg Arg Asp Leu Gly Leu Pro Pro Asp Ser
                165                 170                 175

Thr Ser Thr Val Leu Ser Ser Glu Leu Glu Ser Ser Ser Phe Ile Asp
            180                 185                 190

Ser Asp Glu Asp Asp Asn Thr Ser Arg Leu Ser Ser Ser Thr Glu Gln
        195                 200                 205

Ser Thr Ser Ser Arg Leu Ile Arg Lys His Lys Arg Arg Arg Lys
210                 215                 220

Gln Arg Met Arg Gln Thr Asp Arg Ala Ser Ser Phe Ser Ser Ile Thr
225                 230                 235                 240

Asp Ser Thr Met Ser Leu Asn Ile Ile Thr Val Thr Leu Asn Met Glu
                245                 250                 255

Arg His His Phe Leu Gly Ile Ser Ile Val Gly Gln Ser Asn Asp Arg
                260                 265                 270

Gly Asp Ala Gly Ile Tyr Leu Arg Leu His Lys Gly Gly Ala Val Ala
        275                 280                 285

Arg Arg Trp Pro Ala Ile Glu Pro Gly Asp Met Leu Leu Ala Gly Ala
        290                 295                 300

Arg Val Ala Arg Glu Leu Ala Glu Gly Pro Glu Leu Thr Gln Ser Pro
305                 310                 315                 320

Ile Asp Pro Ala Ala Trp Val Ser His Thr Ala Ala Leu Thr Gly Ala
                325                 330                 335

Leu Pro Arg Tyr Gly Thr Ser Pro Cys Ser Ser Ala Val Ser Arg Thr
                340                 345                 350

Ser Ser Ser Ser Leu Thr Ser Ser Val Pro Gly Ala Ala Gln Leu Glu
        355                 360                 365

Glu Ala Pro Leu Thr Val Lys Ser Asp Met Gly Ala Ile Val Arg Val
        370                 375                 380

Met Gln Leu Pro Asp Ser Gly Leu Glu Ile Arg Asp Arg Met Trp Leu
385                 390                 395                 400

Lys Ile Thr Ile Ala Asn Ala Val Ile Gly Ala Asp Val Val Asp Trp
                405                 410                 415

Leu Tyr Thr His Val Glu Gly Phe Lys Glu Arg Arg Glu Ala Arg Lys
                420                 425                 430

Tyr Ala Ser Ser Met Leu Lys Arg Gly Phe Leu Arg His Thr Val Asn
```

```
            435                 440                 445
Lys Ile Thr Phe Ser Glu Gln Cys Tyr Tyr Val Phe Gly Asp Leu Cys
    450                 455                 460

Ser Asn Leu Ala Ala Leu Asn Leu Asn Ser Gly Ser Ser Gly Ala Ser
465                 470                 475                 480

Glu Gln Asp Thr Leu Ala Pro Leu Pro His Pro Ala Ala Pro Trp Pro
                485                 490                 495

Leu Gly Gln Gly Tyr Pro Tyr Gln Tyr Pro Gly Pro Pro Cys Phe
            500                 505                 510

Pro Pro Ala Tyr Gln Asp Pro Ser Phe Ser Tyr Gly Ser Gly Ser Ala
                515                 520                 525

Gly Ser Gln Gln Ser Glu Gly Ser Lys Ser Ser Gly Ser Thr Arg Ser
    530                 535                 540

Ala Gly Gly Ser Ser Arg Arg Ala Leu Gly Arg Glu Lys Glu His Arg
545                 550                 555                 560

Ala Ala Gly Ala Gly Gly Ser Gly Ser Glu Ser Asp His Thr Ala Pro
                565                 570                 575

Ser Gly Val Gly Gly Ser Gly Trp Arg Glu Arg Pro Ala Ser Gln Leu
            580                 585                 590

Ser Cys Gly Ser Ser Pro Arg Ser Gln Ala Ser Ala Ala Pro Gly
                595                 600                 605

Leu Pro Pro Leu His Pro Leu Thr Lys Ala Tyr Ser Val Val Gly Gly
    610                 615                 620

Pro Pro Gly Gly Pro Pro Val Arg Glu Leu Ala Ala Val Pro Pro Glu
625                 630                 635                 640

Leu Thr Gly Ser Arg Gln Ser Phe Gln Lys Ala Met Gly Asn Pro Cys
                645                 650                 655

Glu Phe Phe Val Asp Ile Met
            660

<210> SEQ ID NO 16
<211> LENGTH: 130
<212> TYPE: PRT
<213> ORGANISM: Equus caballus

<400> SEQUENCE: 16

Met Leu Tyr Leu Tyr Gly Pro Glu Arg Pro Gly Leu Pro Leu Ala Phe
1               5                   10                  15

Ala Pro Ala Ala Ala Leu Ala Ala Ser Gly Arg Ala Glu Pro Pro Gln
                20                  25                  30

Lys Pro Pro Tyr Ser Tyr Ile Ala Leu Ile Ala Met Ala Ile Gln Asp
            35                  40                  45

Ala Pro Glu Gln Arg Val Thr Leu Asn Gly Ile Tyr Gln Phe Ile Met
    50                  55                  60

Asp Arg Phe Pro Phe Tyr His Asp Asn Arg Gln Gly Trp Gln Asn Ser
65                  70                  75                  80

Ile Arg His Asn Leu Ser Leu Asn Asp Cys Phe Val Lys Val Pro Arg
                85                  90                  95

Glu Lys Gly Arg Pro Gly Lys Gly Ser Tyr Trp Thr Leu Asp Pro Arg
            100                 105                 110

Cys Leu Asp Met Phe Glu Asn Gly Asn Tyr Arg Arg Arg Lys Arg Lys
    115                 120                 125

Pro Lys
    130
```

<210> SEQ ID NO 17
<211> LENGTH: 346
<212> TYPE: PRT
<213> ORGANISM: Equus caballus

<400> SEQUENCE: 17

Ser Ala Leu Gly Ala Val Ala Leu Leu Trp Gly Gln Leu Phe
1               5                   10                  15

Ala Val Asp Thr Gly Asn Glu Ala Thr Asp Phe Thr Asp Asp Ser Cys
            20                  25                  30

Pro Lys Pro Pro Glu Ile Pro Asn Gly Tyr Val Glu His Leu Val Arg
        35                  40                  45

Tyr Gln Cys Lys Asn Tyr Tyr Arg Leu Arg Ser Glu Gly Asp Gly Val
    50                  55                  60

Tyr Ala Leu Asn Ser Glu Lys Gln Trp Val Asn Lys Ala Ser Gly Thr
65                  70                  75                  80

Lys Leu Pro Glu Cys Glu Ala Val Cys Gly Lys Pro Lys Asn Pro Val
                85                  90                  95

Asp Gln Val Gln Arg Ile Ile Gly Gly Leu Leu Asp Ala Lys Gly Ser
            100                 105                 110

Phe Pro Trp Gln Ala Lys Leu Val Ser Arg His Asn Leu Thr Thr Gly
        115                 120                 125

Ala Thr Leu Ile Ser Glu Gln Trp Leu Leu Thr Thr Ala Gln Asn Leu
    130                 135                 140

Phe Leu Asn His Thr Pro Asp Ala Lys Pro Lys Asp Ile Ala Pro Thr
145                 150                 155                 160

Leu Lys Leu Tyr Val Gly Arg Lys Gln Pro Val Glu Ile Glu Lys Val
                165                 170                 175

Val Phe His Pro Asp Tyr Gln Glu Val Asp Ile Gly Leu Ile Lys Leu
            180                 185                 190

Lys Glu Lys Val Pro Val Gly Glu Arg Val Met Pro Ile Cys Leu Pro
        195                 200                 205

Ser Lys Asp Tyr Ala Gln Val Gly Arg Val Gly Tyr Val Ser Gly Trp
    210                 215                 220

Gly Arg Asn Ala Asn Phe Asn Phe Thr Glu Leu Leu Lys Tyr Val Thr
225                 230                 235                 240

Leu Pro Val Ala Asp Gln Asp Thr Cys Val Lys His Tyr Glu Gly Ser
                245                 250                 255

Thr Val Pro Glu Lys Lys Thr Asn Arg Ser Ser Val Gly Val Gln Pro
            260                 265                 270

Ile Leu Asn Glu His Thr Phe Cys Ala Gly Leu Ser Lys Phe Gln Glu
        275                 280                 285

Asp Thr Cys Tyr Gly Asp Ala Gly Ser Ala Phe Val Ile His Asp Glu
    290                 295                 300

Glu Asp Asp Thr Trp Tyr Ala Ala Gly Ile Leu Ser Phe Asp Lys Ser
305                 310                 315                 320

Cys Ala Val Ala Glu Tyr Gly Val Tyr Val Lys Val Pro Ser Ile Leu
                325                 330                 335

Asp Trp Val Gln Lys Thr Ile Ala Glu Asn
            340                 345

<210> SEQ ID NO 18
<211> LENGTH: 155
<212> TYPE: PRT
<213> ORGANISM: Equus caballus

<400> SEQUENCE: 18

```
Gly Gly Glu Leu Lys Val Lys Met Leu Gly Gly Glu Phe Leu Val Pro
1               5                   10                  15

Leu Lys Asp Ser Met Leu Val Ser Glu Leu Lys Gln Gln Ile Ala Gln
            20                  25                  30

Lys Thr Gly Val Pro Pro Phe Gln Gln Arg Leu Ala Thr His Pro Ala
        35                  40                  45

Gly Met Val Leu Gln Asp Arg Val Pro Leu Val Ser Gln Gly Leu Gly
    50                  55                  60

Pro Gly Ser Thr Val Val Leu Val Gln Asn Cys Asp Thr Pro Leu
65                  70                  75                  80

Ser Ile Leu Val Arg Asn Gly Lys Gly Arg Ser Ser Ala Tyr Glu Val
                85                  90                  95

Arg Leu Thr Gln Thr Val Ala Glu Leu Lys Gln Gln Val Cys Leu Arg
            100                 105                 110

Glu Ser Val Gln Ala Asp Gln Phe Trp Leu Thr Phe Glu Gly Lys Pro
        115                 120                 125

Met Asp Asp Gln Leu His Leu Gly Glu Tyr Glu Leu Thr Ala Gly Cys
    130                 135                 140

Thr Val Tyr Met Asn Leu Arg Leu Arg Gly Gly
145                 150                 155
```

<210> SEQ ID NO 19
<211> LENGTH: 761
<212> TYPE: PRT
<213> ORGANISM: Equus caballus

<400> SEQUENCE: 19

```
Ser Ser Lys Ser Asn Met Leu Arg Gly Arg Asn Ser Ala Thr Ser Ala
1               5                   10                  15

Asp Glu Gln Pro His Ile Gly Asn Tyr Arg Leu Leu Lys Thr Ile Gly
            20                  25                  30

Lys Gly Asn Phe Ala Lys Val Lys Leu Ala Arg His Ile Leu Thr Gly
        35                  40                  45

Lys Glu Val Ala Val Lys Ile Ile Asp Lys Thr Gln Leu Asn Ser Ser
    50                  55                  60

Ser Leu Gln Lys Leu Phe Arg Glu Val Arg Ile Met Lys Val Leu Asn
65                  70                  75                  80

His Pro Asn Ile Val Lys Leu Phe Glu Val Ile Glu Thr Glu Lys Thr
                85                  90                  95

Leu Tyr Leu Val Met Glu Tyr Ala Ser Gly Gly Glu Val Phe Asp Tyr
            100                 105                 110

Leu Val Ala His Gly Arg Met Lys Glu Lys Glu Ala Arg Ala Lys Phe
        115                 120                 125

Arg Gln Ile Val Ser Ala Val Gln Tyr Cys His Gln Lys Phe Ile Val
    130                 135                 140

His Arg Asp Leu Lys Ala Glu Asn Leu Leu Leu Asp Ala Asp Met Asn
145                 150                 155                 160

Ile Lys Ile Ala Asp Phe Gly Phe Ser Asn Glu Phe Thr Phe Gly Asn
                165                 170                 175

Lys Leu Asp Thr Phe Cys Gly Ser Pro Pro Tyr Ala Ala Pro Glu Leu
            180                 185                 190

Phe Gln Gly Lys Lys Tyr Asp Gly Pro Glu Val Asp Val Trp Ser Leu
        195                 200                 205
```

```
Gly Val Ile Leu Tyr Thr Leu Val Ser Gly Leu Pro Phe Asp Gly
    210                 215                 220

Gln Asn Leu Lys Glu Leu Arg Glu Arg Val Leu Arg Gly Lys Tyr Arg
225                 230                 235                 240

Ile Pro Phe Tyr Met Ser Thr Asp Cys Glu Asn Leu Leu Lys Lys Phe
                245                 250                 255

Leu Ile Leu Asn Pro Ser Lys Arg Gly Thr Leu Glu Gln Ile Met Lys
                260                 265                 270

Asp Arg Trp Met Asn Val Gly His Glu Asp Asp Glu Leu Lys Pro Tyr
                275                 280                 285

Val Glu Pro Leu Pro Asp Tyr Lys Asp Pro Arg Arg Thr Glu Leu Met
290                 295                 300

Val Ser Met Gly Tyr Thr Arg Glu Glu Ile Gln Asp Ser Leu Val Gly
305                 310                 315                 320

Gln Arg Tyr Asn Glu Val Met Ala Thr Tyr Leu Leu Leu Gly Tyr Lys
                325                 330                 335

Ser Ser Glu Leu Glu Gly Asp Thr Ile Thr Leu Lys Pro Arg Pro Pro
                340                 345                 350

Ala Asp Leu Thr Asn Ser Ser Ala Pro Ser Pro Ser His Lys Val Gln
                355                 360                 365

Arg Ser Val Ser Ala Asn Pro Lys Gln Arg Arg Phe Ser Asp Gln Ala
370                 375                 380

Gly Pro Ala Ile Pro Thr Ser Asn Ser Tyr Ser Lys Lys Thr Gln Ser
385                 390                 395                 400

Asn Asn Ala Glu Asn Lys Arg Pro Glu Glu Asp Arg Glu Ser Gly Arg
                405                 410                 415

Lys Ala Ser Ser Thr Ala Lys Val Pro Ala Ser Pro Leu Pro Gly Leu
                420                 425                 430

Glu Arg Lys Lys Thr Thr Pro Thr Pro Ser Thr Asn Ser Val Leu Ser
                435                 440                 445

Thr Ser Thr Asn Arg Ser Arg Asn Ser Pro Leu Leu Glu Arg Ala Ser
    450                 455                 460

Leu Gly Gln Ala Ser Ile Gln Asn Gly Lys Asp Ser Leu Thr Met Pro
465                 470                 475                 480

Gly Ser Arg Ala Ser Thr Ala Ser Ala Ser Ala Val Ser Ala Ala
                485                 490                 495

Arg Pro Arg Gln His Gln Lys Ser Met Ser Ala Ser Val His Pro Asn
                500                 505                 510

Lys Ala Thr Gly Leu Pro Pro Thr Asp Ser Asn Cys Glu Val Pro Arg
                515                 520                 525

Pro Arg Gln Val Thr Ala Pro Gln Arg Val Pro Val Ala Ser Pro Ser
530                 535                 540

Ala His Asn Ile Ser Ser Ser Gly Gly Ala Pro Asp Arg Thr Asn Phe
545                 550                 555                 560

Pro Arg Gly Val Ser Ser Arg Ser Thr Phe His Ala Gly Gln Leu Arg
                565                 570                 575

Gln Val Arg Asp Gln Gln Asn Leu Pro Tyr Gly Val Thr Pro Ala Ser
                580                 585                 590

Pro Ser Gly Asn Ser Gln Gly Arg Arg Gly Ala Ser Gly Ser Ile Phe
                595                 600                 605

Ser Lys Phe Thr Ser Lys Phe Val Arg Arg Asn Leu Ser Phe Arg Phe
                610                 615                 620
```

Ala Arg Arg Asn Leu Asn Glu Pro Glu Ser Lys Asp Arg Val Glu Thr
625                 630                 635                 640

Leu Arg Pro His Val Val Gly Ser Gly Gly Asn Asp Lys Glu Lys Glu
            645                 650                 655

Glu Phe Arg Glu Ala Lys Pro Arg Ser Leu Arg Phe Thr Trp Ser Met
        660                 665                 670

Lys Thr Thr Ser Ser Met Glu Pro Asn Glu Met Met Arg Glu Ile Arg
            675                 680                 685

Lys Val Leu Asp Ala Asn Ser Cys Gln Ser Glu Leu His Glu Lys Tyr
        690                 695                 700

Met Leu Leu Cys Met His Gly Thr Pro Gly His Glu Asn Phe Val Gln
705                 710                 715                 720

Trp Glu Met Glu Val Cys Lys Leu Pro Arg Leu Ser Leu Asn Gly Val
            725                 730                 735

Arg Phe Lys Arg Ile Ser Gly Thr Ser Met Ala Phe Lys Asn Ile Ala
        740                 745                 750

Ser Lys Ile Ala Asn Glu Leu Lys Leu
        755                 760

<210> SEQ ID NO 20
<211> LENGTH: 589
<212> TYPE: PRT
<213> ORGANISM: Equus caballus

<400> SEQUENCE: 20

Met Ala Ala Ala Asp Gly Asp Asp Ser Leu Tyr Pro Ile Ala Val Leu
1               5                   10                  15

Ile Asp Glu Leu Arg Asn Glu Asp Val Gln Leu Arg Leu Asn Ser Ile
                20                  25                  30

Lys Lys Leu Ser Thr Ile Ala Leu Ala Leu Gly Val Glu Arg Thr Arg
            35                  40                  45

Ser Glu Leu Leu Pro Phe Leu Thr Asp Thr Ile Tyr Asp Glu Asp Glu
        50                  55                  60

Val Leu Leu Ala Leu Ala Glu Gln Leu Gly Thr Phe Thr Thr Leu Val
65                  70                  75                  80

Gly Gly Pro Glu Tyr Val His Cys Leu Leu Pro Pro Leu Glu Ser Leu
                85                  90                  95

Ala Thr Val Glu Glu Thr Val Val Arg Asp Lys Ala Val Glu Ser Leu
            100                 105                 110

Arg Ala Ile Ser His Glu His Ser Pro Ser Asp Leu Glu Ala His Phe
        115                 120                 125

Val Pro Leu Val Lys Arg Leu Ala Gly Gly Asp Trp Phe Thr Ser Arg
130                 135                 140

Thr Ser Ala Cys Gly Leu Phe Ser Val Cys Tyr Pro Arg Val Ser Ser
145                 150                 155                 160

Ala Val Lys Ala Glu Leu Arg Gln Tyr Phe Arg Asn Leu Cys Ser Asp
                165                 170                 175

Asp Thr Pro Met Val Arg Arg Ala Ala Ala Ser Lys Leu Gly Glu Phe
            180                 185                 190

Ala Lys Val Leu Glu Leu Asp Asn Val Lys Ser Glu Ile Ile Pro Met
        195                 200                 205

Phe Ser Asn Leu Ala Ser Asp Glu Gln Asp Ser Val Arg Leu Leu Ala
        210                 215                 220

Val Glu Ala Cys Val Asn Ile Ala Gln Leu Leu Pro Gln Glu Asp Leu
225                 230                 235                 240

Glu Ala Leu Val Met Pro Thr Leu Arg Gln Ala Ala Glu Asp Lys Ser
                245                 250                 255

Trp Arg Val Arg Tyr Met Val Ala Asp Lys Phe Thr Glu Leu Gln Lys
            260                 265                 270

Ala Val Gly Pro Glu Ile Thr Lys Thr Asp Leu Val Pro Ala Phe Gln
        275                 280                 285

Asn Leu Met Lys Asp Cys Glu Ala Glu Val Arg Ala Ala Ser His
    290                 295                 300

Lys Val Lys Glu Phe Cys Glu Asn Leu Ser Ala Asp Cys Arg Glu Asn
305                 310                 315                 320

Val Ile Met Thr Gln Ile Leu Pro Cys Ile Lys Glu Leu Val Ser Asp
                325                 330                 335

Ala Asn Gln His Val Lys Ser Ala Leu Ala Ser Val Ile Met Gly Leu
            340                 345                 350

Ser Pro Ile Leu Gly Lys Asp Asn Thr Ile Glu His Leu Leu Pro Leu
        355                 360                 365

Phe Leu Ala Gln Leu Lys Asp Glu Cys Pro Glu Val Arg Leu Asn Ile
    370                 375                 380

Ile Ser Asn Leu Asp Cys Val Asn Glu Val Ile Gly Ile Arg Gln Leu
385                 390                 395                 400

Ser Gln Ser Leu Leu Pro Ala Ile Val Glu Leu Ala Glu Asp Ala Lys
                405                 410                 415

Trp Arg Val Arg Leu Ala Ile Ile Glu Tyr Met Pro Leu Leu Ala Gly
            420                 425                 430

Gln Leu Gly Val Glu Phe Phe Asp Glu Lys Leu Asn Ser Leu Cys Met
        435                 440                 445

Ala Trp Leu Val Asp His Val Tyr Ala Ile Arg Glu Ala Ala Thr Ser
    450                 455                 460

Asn Leu Lys Lys Leu Val Glu Lys Phe Gly Lys Glu Trp Ala His Ala
465                 470                 475                 480

Thr Ile Ile Pro Lys Val Leu Ala Met Ser Gly Asp Pro Asn Tyr Leu
                485                 490                 495

His Arg Met Thr Thr Leu Phe Cys Ile Asn Val Leu Ser Glu Val Cys
            500                 505                 510

Gly Gln Asp Ile Thr Thr Lys His Met Leu Pro Thr Val Leu Arg Met
        515                 520                 525

Ala Gly Asp Pro Val Ala Asn Val Arg Phe Asn Val Ala Lys Ser Leu
    530                 535                 540

Gln Lys Ile Gly Pro Ile Leu Asp Asn Ser Thr Leu Gln Ser Glu Val
545                 550                 555                 560

Lys Pro Ile Leu Glu Lys Leu Thr Gln Asp Gln Asp Val Asp Val Lys
                565                 570                 575

Tyr Phe Ala Gln Glu Ala Leu Thr Val Leu Ser Leu Ala
            580                 585

<210> SEQ ID NO 21
<211> LENGTH: 589
<212> TYPE: PRT
<213> ORGANISM: Equus caballus

<400> SEQUENCE: 21

Met Ala Ala Ala Asp Gly Asp Asp Ser Leu Tyr Pro Ile Ala Val Leu
1               5                   10                  15

Ile Asp Glu Leu Arg Asn Glu Asp Val Gln Leu Arg Leu Asn Ser Ile

```
                20                  25                  30
Lys Lys Leu Ser Thr Ile Ala Leu Ala Leu Gly Val Glu Arg Thr Arg
            35                  40                  45

Ser Glu Leu Leu Pro Phe Leu Thr Asp Thr Ile Tyr Asp Glu Asp Glu
        50                  55                  60

Val Leu Leu Ala Leu Ala Glu Gln Leu Gly Thr Phe Thr Thr Leu Val
65                  70                  75                  80

Gly Gly Pro Glu Tyr Val His Cys Leu Leu Pro Pro Leu Glu Ser Leu
                85                  90                  95

Ala Thr Val Glu Glu Thr Val Arg Asp Lys Ala Val Glu Ser Leu
            100                 105                 110

Arg Ala Ile Ser His Glu His Ser Pro Ser Asp Leu Glu Ala His Phe
            115                 120                 125

Val Pro Leu Val Lys Arg Leu Ala Gly Gly Asp Trp Phe Thr Ser Arg
        130                 135                 140

Thr Ser Ala Cys Gly Leu Phe Ser Val Cys Tyr Pro Arg Val Ser Ser
145                 150                 155                 160

Ala Val Lys Ala Glu Leu Arg Gln Tyr Phe Arg Asn Leu Cys Ser Asp
                165                 170                 175

Asp Thr Pro Met Val Arg Arg Ala Ala Ala Ser Lys Leu Gly Glu Phe
            180                 185                 190

Ala Lys Val Leu Glu Leu Asp Asn Val Lys Ser Glu Ile Ile Pro Met
        195                 200                 205

Phe Ser Asn Leu Ala Ser Asp Glu Gln Asp Ser Val Arg Leu Leu Ala
210                 215                 220

Val Glu Ala Cys Val Asn Ile Ala Gln Leu Leu Pro Gln Glu Asp Leu
225                 230                 235                 240

Glu Ala Leu Val Met Pro Thr Leu Arg Gln Ala Ala Glu Asp Lys Ser
                245                 250                 255

Trp Arg Val Arg Tyr Met Val Ala Asp Lys Phe Thr Glu Leu Gln Lys
            260                 265                 270

Ala Val Gly Pro Glu Ile Thr Lys Thr Asp Leu Val Pro Ala Phe Gln
        275                 280                 285

Asn Leu Met Lys Asp Cys Glu Ala Glu Val Arg Ala Ala Ala Ser His
290                 295                 300

Lys Val Lys Glu Phe Cys Glu Asn Leu Ser Ala Asp Cys Arg Glu Asn
305                 310                 315                 320

Val Ile Met Thr Gln Ile Leu Pro Cys Ile Lys Glu Leu Val Ser Asp
                325                 330                 335

Ala Asn Gln His Val Lys Ser Ala Leu Ala Ser Val Ile Met Gly Leu
            340                 345                 350

Ser Pro Ile Leu Gly Lys Asp Asn Thr Ile Glu His Leu Leu Pro Leu
        355                 360                 365

Phe Leu Ala Gln Leu Lys Asp Glu Cys Pro Glu Val Arg Leu Asn Ile
370                 375                 380

Ile Ser Asn Leu Asp Cys Val Asn Glu Val Ile Gly Ile Arg Gln Leu
385                 390                 395                 400

Ser Gln Ser Leu Leu Pro Ala Ile Val Glu Leu Ala Glu Asp Ala Lys
                405                 410                 415

Trp Arg Val Arg Leu Ala Ile Ile Glu Tyr Met Pro Leu Leu Ala Gly
            420                 425                 430

Gln Leu Gly Val Glu Phe Phe Asp Glu Lys Leu Asn Ser Leu Cys Met
        435                 440                 445
```

Ala Trp Leu Val Asp His Val Tyr Ala Ile Arg Glu Ala Ala Thr Ser
    450                 455                 460

Asn Leu Lys Lys Leu Val Glu Lys Phe Gly Lys Glu Trp Ala His Ala
465                 470                 475                 480

Thr Ile Ile Pro Lys Val Leu Ala Met Ser Gly Asp Pro Asn Tyr Leu
                485                 490                 495

His Arg Met Thr Thr Leu Phe Cys Ile Asn Val Leu Ser Glu Val Cys
            500                 505                 510

Gly Gln Asp Ile Thr Thr Lys His Met Leu Pro Thr Val Leu Arg Met
        515                 520                 525

Ala Gly Asp Pro Val Ala Asn Val Arg Phe Asn Val Ala Lys Ser Leu
    530                 535                 540

Gln Lys Ile Gly Pro Ile Leu Asp Asn Ser Thr Leu Gln Ser Glu Val
545                 550                 555                 560

Lys Pro Ile Leu Glu Lys Leu Thr Gln Asp Gln Asp Val Asp Val Lys
                565                 570                 575

Tyr Phe Ala Gln Glu Ala Leu Thr Val Leu Ser Leu Ala
            580                 585

<210> SEQ ID NO 22
<211> LENGTH: 1511
<212> TYPE: PRT
<213> ORGANISM: Equus caballus

<400> SEQUENCE: 22

Met Pro Leu Phe Glu Leu Ser Arg Met Asp Ser Pro Pro Lys Leu Thr
1               5                   10                  15

Gly Glu Thr Leu Ile Val His His Ile Pro Leu Val His Cys Gln Val
                20                  25                  30

Pro Asp Arg Gln Cys Arg Gly Gly Ala Ser Gly Gly Ser Gly Ser Thr
            35                  40                  45

Arg Pro Asn Pro Phe Cys Pro Ser Glu Leu Gly Ile Thr Lys Pro Asp
        50                  55                  60

Gln Asp Leu Gly Gln Ala Asp Ser Leu Leu Tyr Asn Ser Arg His Ser
65                  70                  75                  80

Ser Thr Gly Gly Ser Ala Arg Ser Ala Asp Ser Thr Lys Ser Arg Gly
                85                  90                  95

Arg Asp Gly Arg Gly Pro Gly Ala Pro Lys Arg His Asn Pro Phe Leu
            100                 105                 110

Gln Gln Glu Gly Val Ala Glu Pro Gly Phe Gly Asp Leu Tyr Glu Asp
        115                 120                 125

Ser Ile Gly Asp Ser Ala Thr Gln Gln Gln Ser Phe His Leu His Gly
    130                 135                 140

Ala Gly Gln Pro Thr Phe Gln Leu Ser Ser Phe Gln Leu Pro Pro Thr
145                 150                 155                 160

Gly Pro Arg Val Gly Arg Pro Trp Gly Thr Arg Arg Ser Arg Ala Gly
                165                 170                 175

Val Val Glu Gly Gln Glu Gln Gln Pro Val Thr Thr Leu Asp Thr Gln
            180                 185                 190

Glu Cys Ser Thr Ser Tyr Cys Cys Arg Pro Glu Leu Glu Ala Glu Thr
        195                 200                 205

Met Glu Leu Asp Glu Cys Gly Gly Pro Gly Gly Ser Gly Ser Gly Gly
    210                 215                 220

Gly Ala Ser Asp Thr Ser Gly Phe Ser Phe Asp Gln Glu Trp Lys Leu

```
            225                 230                 235                 240
Ser Ser Asp Glu Ser Pro Arg Asn Pro Gly Cys Thr Gly Ser Gly Pro
                245                 250                 255

Gln His Cys Arg Cys Ser Ser Thr Ser Ser Gln Ser Glu Thr Ala Asp
                260                 265                 270

Gln Ser Met Gly Tyr Val Ser Asp Ser Ser Cys Asn Ser Ser Asp Gly
                275                 280                 285

Val Leu Val Thr Phe Ser Thr Leu Tyr Asn Lys Met His Gly Asn Ser
290                 295                 300

His Ala Asn Leu Asn Ser Ala Pro Gln Ser Cys Ser Asp Ser Ser Phe
305                 310                 315                 320

Cys Ser His Ser Asp Pro Gly Ala Phe Tyr Leu Asp Leu Gln Thr Phe
                325                 330                 335

Pro Ala Glu Glu Ser His His Pro Asn Asn Gly Gly Arg Glu Gly Gly
                340                 345                 350

Tyr Gly Cys Pro His Ala Ser Ser Pro Glu Leu Asp Ala Asn Cys Asn
                355                 360                 365

Ser Tyr His Pro His Cys Glu Pro Cys Pro Ala Val Ala Asp Leu Thr
                370                 375                 380

Ala Cys Phe Gln Ser Gln Ala Arg Leu Val Val Ala Thr Gln Asn Tyr
385                 390                 395                 400

Tyr Lys Leu Val Thr Cys Asp Leu Ser Ser Gln Ser Ser Pro Ser Pro
                405                 410                 415

Ala Gly Ser Ser Ile Thr Ser Cys Ser Glu Glu His Thr Lys Ile Ser
                420                 425                 430

Pro Ala Pro Gly Pro Gly Pro His Pro Gly Pro Ser Gln Pro Ser Glu
                435                 440                 445

Tyr Tyr Leu Phe Gln Lys Pro Glu Val Gln Pro Glu Gln Glu Ala
                450                 455                 460

Gly Gly Ser Ser Glu Glu Ala Ala Ala Pro Val Gly Pro Ala Met Ile
465                 470                 475                 480

Glu Gly Gln Val Tyr Thr Asn Thr Ser Pro Pro Asn Leu Ser Thr Gly
                485                 490                 495

Arg Gln Arg Ser Arg Ser Tyr Asp Arg Ser Leu Glu Arg Ser Pro Pro
                500                 505                 510

Val Arg Leu Gly Ser Leu Glu Arg Met Leu Ser Cys Pro Val Arg Leu
                515                 520                 525

Ser Glu Gly Pro Ala Ala Leu Ala Gly Pro Ser Ser Pro Pro Arg Arg
                530                 535                 540

Val Thr Ser Phe Ala Glu Leu Ala Lys Gly Arg Lys Lys Ala Ala Gly
545                 550                 555                 560

Ser Gly Ser Pro Pro Leu Arg Val Ser Ile Gly Asp Ser Ser Gln Asp
                565                 570                 575

Phe Ser Pro Ile Gln Glu Thr Gln Gln Asp Arg Val Gly Pro Leu Asp
                580                 585                 590

Lys Gly Thr Arg Cys Ser His Ser Leu Pro Pro Met Pro Leu Gly Pro
                595                 600                 605

Gly Met Asp Leu Leu Asp Pro Glu Pro Trp Ser Thr Gln Val Cys Gln
                610                 615                 620

Gly Pro Gln Ser Ser Glu Met Pro Ser Ala Gly Leu Arg Ala Ala Glu
625                 630                 635                 640

Gln Gly Pro Leu Ala Gln Leu Met Asp Pro Gly Pro Ala Leu Pro Gly
                645                 650                 655
```

-continued

Ser Pro Ala Asn Ser His Pro Gln Arg Asp Ala Arg Ala Arg Ala Asp
            660                 665                 670

Gly Gly Gly Ala Glu Ser Arg Pro Val Leu Arg Tyr Ser Lys Glu Gln
            675                 680                 685

Arg Pro Thr Thr Leu Pro Ile Gln Pro Phe Val Phe Gln His His Phe
    690                 695                 700

Pro Lys Gln Leu Ala Lys Ala Arg Ala Leu His Ser Leu Ser Gln Leu
705                 710                 715                 720

Tyr Ser Leu Ser Gly Cys Ser Arg Ala Gln Gln Pro Ala Pro Leu Ala
                725                 730                 735

Ala Pro Thr Ala Gln Val Pro Ala Pro Ala Pro Ser Gly Glu Ser Gln
            740                 745                 750

Ala Ser Ala Asn Lys Gly Ala Gly Lys Ala Gly Pro Glu Pro Glu Thr
            755                 760                 765

Ser Arg Pro Ser Pro Leu Gly Ser Tyr Ser Pro Ile Arg Ser Ala Gly
            770                 775                 780

Pro Phe Gly Pro Ser Thr Asp Ser Ser Pro Ser Thr Ser Cys Ser Pro
785                 790                 795                 800

Pro Leu Glu Gln Ala Thr Ala Thr Glu Ser Pro Pro Trp Ser His
            805                 810                 815

Ser Cys Pro Pro Ala Val Arg Pro Ala Thr Ser Gln Gln Pro Pro Lys
            820                 825                 830

Glu Asp Gln Lys Ile Leu Thr Leu Ala Glu Tyr Arg Leu His Gly Thr
            835                 840                 845

Gly Ser Leu Pro Pro Leu Gly Ser Trp Arg Ser Gly Phe Ser Arg Ala
    850                 855                 860

Glu Ser Leu Ala Arg Gly Gly Glu Gly Ser Met Ala Ser Arg Pro
865                 870                 875                 880

Ser Asn Ala Asn His Leu Ser Pro Gln Ala Leu Lys Trp Arg Glu Tyr
                885                 890                 895

Arg Arg Lys Asn Pro Leu Gly Pro Pro Gly Leu Ser Gly Ser Leu Asp
            900                 905                 910

Arg Arg Pro Gln Glu Ala Arg Leu Ala Arg Arg Asn Pro Ile Phe Glu
            915                 920                 925

Phe Pro Gly Ser Leu Ser Ala Ala Gly His Leu Asn Cys Arg Leu Asn
    930                 935                 940

Gly Gln Val Val Lys Pro Leu Pro Leu Thr Cys Pro Asp Phe Gln Asp
945                 950                 955                 960

Pro Phe Ser Leu Thr Glu Lys Pro Pro Ala Glu Phe Cys Leu Ser Pro
            965                 970                 975

Asp Gly Asn Ser Glu Ala Ile Ser Ile Asp Leu Leu Gln Lys Lys Gly
            980                 985                 990

Leu Val Lys Ala Val Asn Thr Ala Val Asp Leu Ile Val Ala His Phe
    995                 1000                1005

Gly Thr Ser Arg Asp Pro Gly Val Lys Ala Lys Leu Gly Asn Ser
    1010                1015                1020

Ser Val Ser Pro Asn Val Gly His Leu Val Leu Lys Tyr Leu Cys
    1025                1030                1035

Pro Ala Val Arg Ala Val Leu Glu Asp Gly Leu Lys Ala Phe Val
    1040                1045                1050

Leu Asp Val Ile Ile Gly Gln Arg Lys Asn Met Pro Trp Ser Val
    1055                1060                1065

-continued

```
Val Glu Ala Ser Thr Gln Leu Gly Pro Ser Thr Lys Val Leu His
1070                1075                1080

Gly Leu Tyr Asn Lys Val Ser Gln Phe Pro Glu Leu Thr Ser His
    1085                1090                1095

Thr Met Arg Phe Asn Ala Phe Ile Leu Gly Leu Leu Asn Ile Arg
    1100                1105                1110

Ser Leu Glu Phe Trp Phe Asn His Leu Tyr Asn His Glu Asp Ile
    1115                1120                1125

Ile Gln Thr His Tyr Gln Pro Trp Gly Phe Leu Ser Ala Ala His
    1130                1135                1140

Thr Val Cys Pro Gly Leu Phe Glu Glu Leu Leu Leu Leu Leu Gln
    1145                1150                1155

Pro Leu Ala Leu Leu Pro Phe Ser Leu Asp Leu Leu Phe Gln His
    1160                1165                1170

Arg Leu Leu Gln Ser Gly Gln Gln Arg Gln His Lys Glu Leu
    1175                1180                1185

Leu Arg Val Ser Gln Asp Leu Leu Leu Ser Ala His Ser Thr Leu
    1190                1195                1200

Gln Leu Ala Gln Ala Arg Gly Gln Glu Gly Pro Gly Asp Met Asp
    1205                1210                1215

Arg Ala Ala His Gly Glu Arg Val Lys Gly Val Gly Ala Pro Glu
    1220                1225                1230

Gly Gly Glu Asp Glu Glu Glu Glu Glu Thr Glu Glu Met Ala
    1235                1240                1245

Glu Ala Ala Gly Gly Ser Gly Arg Gly Arg Trp Ala Gln Gly Gly
    1250                1255                1260

Gln Ala Gly Trp Trp Tyr Gln Leu Met Gln Ser Ser Gln Val Tyr
    1265                1270                1275

Ile Asp Gly Ser Thr Glu Gly Ser Arg Phe Pro Arg Gly Gly Ser
    1280                1285                1290

Asn Ser Ser Gly Ser Ser Ser Glu Lys Lys Lys Gly Ala Gly
    1295                1300                1305

Gly Arg Gly Pro Pro Pro Arg Glu Gly Val Val Glu Gly Ala Glu
    1310                1315                1320

Ala Cys Pro Ala Pro Glu Glu Thr Leu Gly Arg Ala Trp Pro Phe
    1325                1330                1335

Trp Met Gly Ser Pro Pro Asp Ser Val Leu Ala Glu Leu Arg Arg
    1340                1345                1350

Ser Arg Glu Arg Glu Gly Ser Thr Ala Pro Pro Ala Glu Asn Glu
    1355                1360                1365

Glu Gly Thr Ser Glu Pro Ser Pro Gly Gly Ile Lys Trp Gly His
    1370                1375                1380

Leu Phe Gly Ser Arg Lys Val Gln Arg Glu Ala Arg Pro Thr Asn
    1385                1390                1395

Arg Leu Pro Ser Asp Trp Leu Ser Leu Asp Lys Ser Met Phe Gln
    1400                1405                1410

Leu Val Val Gln Thr Val Gly Ala Arg Arg Glu Pro Glu Pro Arg
    1415                1420                1425

Glu Ser Leu Gln Glu Pro His Pro Pro Ala Leu Pro Ser Lys Pro
    1430                1435                1440

Pro Cys Lys Val Lys Ala Leu Cys His His Leu Ala Thr Gly Pro
    1445                1450                1455

Gly Gln Leu Ser Phe His Lys Gly Asp Ile Leu Arg Val Leu Gly
```

```
            1460                1465                1470
Pro Ala Lys Gly Asp Trp Leu His Cys Ser Arg Gly Thr Asp Met
        1475                1480                1485

Gly Leu Val Pro Leu Ala Tyr Val Thr Leu Thr Pro Thr Pro Ser
    1490                1495                1500

Pro Thr Pro Gly Ser Ser Gln Asn
    1505                1510
```

<210> SEQ ID NO 23
<211> LENGTH: 479
<212> TYPE: PRT
<213> ORGANISM: Equus caballus

<400> SEQUENCE: 23

```
Pro Pro Thr Gly Thr Met Thr Pro Thr Arg Thr Gln His Ser Leu Ala
1               5                  10                  15

Gly Gln Thr Tyr Met Val Pro Leu Ile Gln Pro Asp Leu Arg Arg Glu
            20                  25                  30

Glu Ala Ile Gln Gln Val Ala Asp Ala Leu Gln Tyr Leu Gln Lys Val
        35                  40                  45

Ser Gly Asp Ile Phe Ser Arg Ile Ser Gln Arg Val Glu Leu Ser Arg
    50                  55                  60

Ser Gln Leu Gln Ala Ile Gly Glu Arg Val Ser Leu Ala Gln Ala Lys
65                  70                  75                  80

Ile Glu Lys Ile Lys Gly Ser Lys Lys Ala Ile Lys Val Phe Ser Ser
                85                  90                  95

Ala Lys Tyr Pro Ala Pro Glu Arg Leu Gln Glu Tyr Gly Ser Ile Phe
            100                 105                 110

Thr Gly Ala Gln Asp Pro Gly Leu Gln Arg Arg Pro Arg Tyr Arg Ile
        115                 120                 125

Gln Ser Lys His Arg Pro Leu Asp Glu Arg Ala Leu Gln Glu Lys Leu
    130                 135                 140

Lys Tyr Phe Pro Val Cys Val Asn Thr Lys Leu Glu Pro Glu Asp Glu
145                 150                 155                 160

Ala Glu Glu Gly Leu Gly Gly Leu Pro Ser Asn Ile Ser Ser Val Ser
                165                 170                 175

Ser Leu Leu Leu Phe Asn Thr Thr Glu Asn Leu Tyr Lys Lys Tyr Val
            180                 185                 190

Phe Leu Asp Pro Leu Ala Gly Ala Val Thr Lys Thr His Val Met Leu
        195                 200                 205

Gly Ala Glu Thr Glu Glu Lys Leu Phe Asp Ala Pro Leu Ser Ile Ser
    210                 215                 220

Lys Arg Glu Gln Leu Glu Gln Gln Val Pro Glu Asn Tyr Phe Tyr Val
225                 230                 235                 240

Pro Asp Leu Gly Gln Val Pro Glu Ile Asp Val Pro Ser Tyr Leu Pro
                245                 250                 255

Asp Leu Pro Gly Ile Ala Asp Asp Leu Met Tyr Ser Ala Asp Leu Gly
            260                 265                 270

Pro Gly Ile Ala Pro Ser Ala Pro Gly Thr Ile Pro Glu Leu Pro Thr
        275                 280                 285

Phe His Thr Glu Val Ala Glu Pro Phe Lys Pro Asp Arg Glu Asp Gly
    290                 295                 300

Val Leu Ile Ala Pro Pro Pro Pro Pro Pro Pro Pro Pro Pro Pro Pro
305                 310                 315                 320
```

```
Ala Pro Ala Val Leu Val Ser Ala Pro Pro Pro Pro Pro Leu
            325                 330                 335

Ser Thr Ala Ser Pro Gly Gln Gly Thr Arg Glu Asp Glu Ser Arg Gly
            340                 345                 350

Gly Val Arg Pro Ser Ala Pro Val Pro Glu Ala Pro Arg Glu Val Val
            355                 360                 365

Glu Pro Ser Ser Gly Arg Ala Thr Leu Leu Glu Ser Ile Arg Gln Ala
370                 375                 380

Gly Gly Ile Gly Lys Ala Lys Leu Arg Ser Val Lys Glu Arg Lys Leu
385                 390                 395                 400

Glu Lys Lys Lys Gln Lys Glu Gln Glu Gln Val Arg Ala Thr Gly Gln
                405                 410                 415

Gly Gly Asp Leu Met Ala Asp Leu Phe Asn Lys Leu Val Met Arg Arg
            420                 425                 430

Lys Gly Ile Ser Gly Lys Gly Pro Ala Pro Gly Ala Ser Glu Gly Pro
            435                 440                 445

Gly Gly Ala Phe Ala Arg Met Ser Asp Ser Ile Pro Pro Leu Pro Pro
            450                 455                 460

Pro Gln Gln Pro Pro Gly Glu Glu Asp Glu Asp Asp Trp Glu Ser
465                 470                 475

<210> SEQ ID NO 24
<211> LENGTH: 835
<212> TYPE: PRT
<213> ORGANISM: Equus caballus

<400> SEQUENCE: 24

Gln Ser Pro Lys Met Ser Val Gln Glu Gln Gly Phe Pro Leu Asp Leu
1               5                   10                  15

Gly Ala Ser Phe Thr Glu Asp Ala Pro Arg Pro Val Pro Gly Glu
            20                  25                  30

Glu Gly Glu Leu Val Ser Thr Asp Pro Arg Pro Val Ser His Ser Phe
            35                  40                  45

Cys Ser Gly Lys Gly Pro Gly Ile Lys Gly Glu Thr Ser Thr Ala Thr
50                  55                  60

Pro Arg Arg Ser Asp Leu Asp Leu Gly Tyr Glu Pro Glu Gly Ser Ala
65                  70                  75                  80

Ser Pro Thr Pro Pro Tyr Leu Lys Trp Ala Glu Ser Leu His Ser Leu
                85                  90                  95

Leu Asp Asp Gln Asp Gly Ile Asn Leu Phe Arg Thr Phe Leu Lys Gln
            100                 105                 110

Glu Asp Cys Ala Asp Leu Leu Asp Phe Trp Phe Ala Cys Ser Gly Phe
            115                 120                 125

Arg Lys Leu Glu Pro Cys Asp Ser Asn Glu Glu Lys Arg Leu Lys Leu
            130                 135                 140

Ala Lys Ala Ile Tyr Arg Lys Tyr Ile Leu Asp Asn Asn Gly Ile Val
145                 150                 155                 160

Ser Arg Gln Thr Lys Pro Ala Thr Lys Ser Phe Ile Lys Asp Cys Ile
                165                 170                 175

Met Lys Gln Leu Ile Asp Pro Ala Met Phe Asp Gln Ala Gln Thr Glu
            180                 185                 190

Ile Gln Ser Thr Met Glu Glu Asn Thr Tyr Pro Ser Phe Leu Lys Ser
            195                 200                 205

Asp Ile Tyr Leu Glu Tyr Thr Arg Thr Gly Ser Glu Ser Pro Lys Leu
210                 215                 220
```

-continued

```
Cys Ser Asp Gln Ser Ser Gly Ser Gly Thr Gly Lys Gly Ile Pro Gly
225                 230                 235                 240

Tyr Leu Pro Thr Leu Asn Glu Asp Glu Glu Trp Lys Cys Asp Gln Asp
            245                 250                 255

Val Asp Glu Asp Asp Gly Arg Asp Pro Gly Pro Gly Arg Leu Thr
        260                 265                 270

Gln Lys Leu Leu Leu Glu Thr Ala Ala Pro Arg Ala Ser Ala Ser Arg
        275                 280                 285

Arg Tyr Ser Glu Gly Arg Glu Phe Arg Tyr Gly Ser Trp Arg Glu Pro
        290                 295                 300

Val Asn Pro Tyr Tyr Val Asn Ser Gly Tyr Ala Leu Ala Pro Ala Thr
305                 310                 315                 320

Ser Ala Asn Asp Ser Glu Gln Gln Ser Leu Ser Ser Asp Ala Asp Ser
                325                 330                 335

Leu Ser Leu Thr Asp Ser Ser Val Asp Gly Val Pro Pro Tyr Arg Ile
            340                 345                 350

Arg Lys Gln His Arg Arg Glu Met Gln Glu Ser Val Gln Val Asn Gly
        355                 360                 365

Arg Val Pro Leu Pro His Ile Pro Arg Thr Tyr Arg Met Pro Lys Glu
370                 375                 380

Ile Arg Val Glu Pro Gln Lys Phe Ala Ala Glu Leu Ile His Arg Leu
385                 390                 395                 400

Glu Ala Ile Gln Arg Thr Arg Glu Ala Glu Lys Leu Glu Glu Arg
            405                 410                 415

Leu Lys Arg Val Arg Met Glu Glu Gly Glu Asp Gly Asp Val Ser
        420                 425                 430

Cys Gly Pro Pro Gly Ala Ser His Lys Leu Pro Ser Ala Pro Ala Trp
        435                 440                 445

His His Phe Pro Pro Arg Tyr Ala Asp Met Gly Cys Thr Gly Leu Arg
        450                 455                 460

Asp Ala His Glu Glu Asn Pro Glu Ser Ile Leu Asp Glu His Val Gln
465                 470                 475                 480

Arg Val Met Arg Thr Pro Gly Cys Gln Ser Pro Gly Pro Gly His Arg
                485                 490                 495

Ser Pro Asp Ser Val His Val Pro Lys Val Pro Gly Val Leu Gly Gly
            500                 505                 510

Ile Ala Pro Gly His Gly Lys His Ala Leu Lys Ser Gly Ala Lys Leu
        515                 520                 525

Asp Ala Ala Gly Leu His Leu His Arg His Ser His His Gly His
        530                 535                 540

His Gly Leu Ala Arg Pro Lys Glu Gln Ala Glu Ala Glu Ala Ala Arg
545                 550                 555                 560

Arg Val Gln Ser Ser Phe Ser Trp Ala Leu Glu Gln His Gly His Thr
                565                 570                 575

Ala Lys Pro Arg Ser His Ser Glu Ser Val Gly Ala Ala His Ile Thr
            580                 585                 590

Ser Asp Gly Leu Thr Tyr Ser Gly Lys Ala Gly Thr Thr Cys Lys Arg
        595                 600                 605

Asn Thr Lys Lys Ala Glu Ser Gly Lys Ser Met Gly Ala Glu Ala Pro
        610                 615                 620

Gly Pro Ser Glu Asp Ala Glu Lys Asn Gln Lys Ile Met Gln Trp Ile
625                 630                 635                 640
```

```
Ile Glu Gly Glu Lys Glu Ile Ser Arg His Arg Lys Ala Gly His Gly
            645                 650                 655

Ser Ser Gly Thr Lys Lys Gln Gln Gly His Glu Ser Ser Arg Pro Leu
            660                 665                 670

Ser Ile Glu Arg Pro Gly Ala Val His Pro Trp Val Ser Ala Gln Leu
            675                 680                 685

Arg Asn Ser Val Gln Pro Ser His Leu Phe Ile Gln Asp Pro Thr Met
        690                 695                 700

Pro Pro Asn Pro Ala Pro Asn Pro Leu Thr Gln Leu Glu Glu Ala Arg
705                 710                 715                 720

Arg Arg Leu Glu Glu Glu Lys Arg Ala Ser Lys Leu Pro Ser Lys
                725                 730                 735

Gln Arg Met Lys Ser Gln Arg Lys Val Gly Ser Ser Thr Gln Pro
            740                 745                 750

Cys Asp Ser Ile Val Val Ala Tyr Tyr Phe Cys Gly Glu Pro Ile Pro
            755                 760                 765

Tyr Arg Thr Leu Val Arg Gly Arg Ala Val Thr Leu Gly Gln Phe Lys
            770                 775                 780

Glu Leu Leu Thr Lys Lys Gly Asn Tyr Arg Tyr Tyr Phe Lys Lys Val
785                 790                 795                 800

Ser Asp Glu Phe Asp Cys Gly Val Val Phe Glu Glu Val Arg Glu Asp
                805                 810                 815

Glu Ala Val Leu Pro Val Phe Glu Glu Lys Ile Ile Gly Lys Val Glu
            820                 825                 830

Lys Val Asp
        835

<210> SEQ ID NO 25
<211> LENGTH: 429
<212> TYPE: PRT
<213> ORGANISM: Equus caballus

<400> SEQUENCE: 25

Val Ala Gly Val Arg Pro Pro Ile Met Asn Gly Pro Met His Pro Arg
1               5                   10                  15

Pro Leu Val Ala Leu Leu Asp Gly Arg Asp Cys Thr Val Glu Met Pro
            20                  25                  30

Ile Leu Lys Asp Val Ala Thr Val Ala Phe Cys Asp Ala Gln Ser Thr
            35                  40                  45

Gln Glu Ile His Glu Lys Val Leu Asn Glu Ala Val Gly Ala Leu Met
        50                  55                  60

Tyr His Thr Ile Thr Leu Thr Arg Glu Asp Leu Glu Lys Phe Lys Ala
65                  70                  75                  80

Leu Arg Ile Ile Val Arg Ile Gly Ser Gly Phe Asp Asn Ile Asp Ile
                85                  90                  95

Lys Ser Ala Gly Asp Leu Gly Ile Ala Val Cys Asn Val Pro Ala Ala
            100                 105                 110

Ser Val Glu Glu Thr Ala Asp Ser Thr Met Cys His Ile Leu Asn Leu
            115                 120                 125

Tyr Arg Arg Thr Thr Trp Leu His Gln Ala Leu Arg Glu Gly Thr Arg
        130                 135                 140

Val Gln Ser Val Glu Gln Ile Arg Glu Val Ala Ser Gly Ala Ala Arg
145                 150                 155                 160

Ile Arg Gly Glu Thr Leu Gly Ile Ile Gly Leu Gly Arg Val Gly Gln
                165                 170                 175
```

```
Ala Val Ala Leu Arg Ala Lys Ala Phe Gly Phe Asn Val Leu Phe Tyr
            180                 185                 190

Asp Pro Tyr Leu Ser Asp Gly Thr Glu Arg Ala Leu Gly Leu Gln Arg
            195                 200                 205

Val Ser Thr Leu Gln Asp Leu Leu Phe His Ser Asp Cys Val Thr Leu
210                 215                 220

His Cys Gly Leu Asn Glu His Asn His His Leu Ile Asn Asp Phe Thr
225                 230                 235                 240

Val Lys Gln Met Arg Gln Gly Ala Phe Leu Val Asn Thr Ala Arg Gly
            245                 250                 255

Gly Leu Val Asp Glu Lys Ala Leu Ala Gln Ala Leu Lys Glu Gly Arg
            260                 265                 270

Ile Arg Gly Ala Ala Leu Asp Val His Glu Ser Glu Pro Phe Ser Phe
            275                 280                 285

Ser Gln Gly Pro Leu Lys Asp Ala Pro Asn Leu Ile Cys Thr Pro His
            290                 295                 300

Ala Ala Trp Tyr Ser Glu Gln Ala Ser Ile Glu Met Arg Glu Glu Ala
305                 310                 315                 320

Ala Arg Glu Ile Arg Arg Ala Ile Thr Gly Arg Ile Pro Asp Ser Leu
            325                 330                 335

Lys Asn Cys Val Asn Lys Asp His Leu Thr Ala Ala Thr His Trp Ala
            340                 345                 350

Ser Met Asp Pro Ala Val Val His Pro Glu Leu Asn Gly Ala Ala Tyr
            355                 360                 365

Arg Tyr Pro Pro Gly Val Val Gly Val Ala Pro Ser Gly Ile Pro Ala
            370                 375                 380

Ala Val Glu Gly Ile Val Pro Ser Ala Met Ser Leu Ser His Gly Leu
385                 390                 395                 400

Pro Pro Val Ser His Pro His Ala Pro Ser Pro Gly Gln Thr Val
            405                 410                 415

Lys Pro Glu Ala Asp Arg Asp His Pro Ser Asp Gln Leu
            420                 425

<210> SEQ ID NO 26
<211> LENGTH: 704
<212> TYPE: PRT
<213> ORGANISM: Equus caballus

<400> SEQUENCE: 26

Met Asp Lys Phe Trp Trp Arg Ala Ala Trp Gly Leu Cys Leu Val Pro
1               5                   10                  15

Leu Ser Leu Ala Gln Ile Asp Leu Asn Ile Thr Cys Arg Tyr Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Gln Lys Ala Leu Asn Ile Gly Phe Glu Thr Cys Arg Tyr Gly
65                  70                  75                  80

Phe Ile Glu Gly His Val Val Ile Pro Arg Ile His Pro Asn Ser Ile
            85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
```

-continued

```
            115                 120                 125
Cys Thr Ser Val Thr Asp Leu Pro Asn Ala Phe Glu Gly Pro Ile Thr
            130                 135                 140
Ile Thr Ile Val Asn Arg Asp Gly Thr Arg Tyr Thr Lys Lys Gly Glu
145                 150                 155                 160
Tyr Arg Thr Asn Pro Glu Asp Ile Asn Pro Ser Thr Pro Ala Asp Asp
                    165                 170                 175
Asp Val Ser Ser Gly Ser Ser Glu Arg Ser Thr Ser Gly Gly Tyr
                    180                 185                 190
Ser Ile Phe His Thr His Leu Pro Thr Thr Arg Pro Thr Gln Asp Gln
                    195                 200                 205
Ser Ser Pro Trp Val Ser Asp Ser Pro Glu Lys Thr Pro Thr Thr Ser
            210                 215                 220
Thr Asp Ser Asn Val Ile Ser Ala Gly Trp Pro Pro Glu Glu Asn
225                 230                 235                 240
Glu Asp Glu Arg Asp Lys His Pro Ser Tyr Ser Gly Ser Gly Ile Asp
                    245                 250                 255
Asp Asp Glu Asp Phe Val Ser Ser Thr Ile Pro Thr Lys Pro Arg Ile
                    260                 265                 270
Phe Lys Phe Pro Glu Val Asn Glu Asp Trp Arg Gln Trp Ser Pro Gly
                    275                 280                 285
His Ser Thr Pro Gly Ile Leu Leu Gln Thr Ala Thr Arg Met Thr Asp
            290                 295                 300
Val Asp Arg Ser Gly Thr Ser Ala Tyr Gly Glu Ser Gln Thr Gln Glu
305                 310                 315                 320
Pro His Ser Pro Leu Val His His Glu His His Asp Glu Glu Glu Thr
                    325                 330                 335
Gln His Ser Thr Ser Ser Thr Trp Ala Leu Ser Ser Arg Thr Ala Glu
                    340                 345                 350
Asp Thr Ala Thr Gln Lys Glu Gln Trp Phe Glu Asp Gly Trp Arg Gly
                    355                 360                 365
Glu Tyr Thr Gln Thr Pro Lys Glu Asp Ser Pro Ser Ala Thr Gly Thr
            370                 375                 380
Ala Val Thr Thr Ala Ser Ala His Asp Ser His Pro Asn Arg Arg Met
385                 390                 395                 400
Thr Thr Gln Ser Gln Glu Asp Ser Ser Trp Thr Tyr Phe Phe Asp Pro
                    405                 410                 415
Ile Ser His Pro Lys Gly Arg Gly His His Thr Glu Arg Trp Met Asp
                    420                 425                 430
Val Asp Ser Ser Arg Ser Thr Thr Leu Gln Pro Ser Ala Asp Pro Ser
                    435                 440                 445
Thr Gly Leu Val Glu Glu Leu Asp Arg Thr Arg Pro Leu Ser Met Thr
            450                 455                 460
Thr Gln Gln Ser His Thr Gln Ser Phe Ser Thr Ser His Gly Gly Leu
465                 470                 475                 480
Glu Glu Asp Lys Asp His Pro Met Thr Ser Thr Pro Ser Ser Ser Asn
                    485                 490                 495
Arg Asn Asp Gly Arg Gly Arg Arg Ser Gly Asn Phe Ser Glu Asp
                    500                 505                 510
Ser Ala Thr Ser Gly Glu Gly Tyr Thr Ala His Ala Pro Asp Thr Lys
            515                 520                 525
Glu Tyr Asn Thr Leu Thr Pro Val Thr Pro Ala Lys Thr Gly Ser Pro
            530                 535                 540
```

```
Gly Val Thr Glu Val Ile Val Leu Asp Asp Ser Asn Ser His Val Asp
545                 550                 555                 560

Gly Ser Phe Ser Gly Asn Leu Ala Thr Tyr Arg Ala Ser Gly Gly Arg
                565                 570                 575

Ala Gln Thr Thr His Gly Ser Glu Thr Ser Gly His Ser Thr Gly Ser
            580                 585                 590

Gln Glu Gly Gly Ala Ser Thr Thr Ser Gly Pro Ile Arg Arg Pro Gln
        595                 600                 605

Ile Pro Glu Trp Leu Ile Ile Leu Ala Ser Leu Leu Ala Leu Ala Leu
        610                 615                 620

Ile Leu Ala Val Cys Ile Ala Val Asn Ser Arg Arg Arg Cys Gly Gln
625                 630                 635                 640

Lys Lys Lys Leu Val Ile Asn Asn Gly Asn Gly Ala Val Asp Asp Arg
                645                 650                 655

Lys Ala Ser Gly Leu Asn Gly Glu Ala Ser Arg Ser Gln Glu Met Val
            660                 665                 670

His Leu Val Asn Lys Glu Ser Ser Glu Thr Gln Asp Gln Phe Met Thr
            675                 680                 685

Ala Asp Glu Thr Arg Asn Leu Gln Asn Val Asp Met Lys Ile Gly Val
            690                 695                 700
```